United States Patent
De La Franier et al.

(10) Patent No.: US 11,543,412 B2
(45) Date of Patent: Jan. 3, 2023

(54) BIOSENSORS AND METHODS FOR DETECTION OF LYSOPHOSPHATIDIC ACID FOR SIGNALING OF OVARIAN CANCER

(71) Applicant: ECONOUS SYSTEMS INC., Mississauga (CA)

(72) Inventors: Brian De La Franier, Toronto (CA); Michael Thompson, Toronto (CA)

(73) Assignee: Thompson Surface Innovations Corporation, Toronto (CA)

( * ) Notice: Subject to any disclaimer, the term of this patent is extended or adjusted under 35 U.S.C. 154(b) by 278 days.

(21) Appl. No.: 16/897,547

(22) Filed: Jun. 10, 2020

(65) Prior Publication Data

US 2020/0300858 A1   Sep. 24, 2020

Related U.S. Application Data

(62) Division of application No. 15/572,295, filed as application No. PCT/CA2016/050545 on May 13, 2016, now abandoned.

(60) Provisional application No. 62/160,800, filed on May 13, 2015.

(51) Int. Cl.
  *G01N 33/574* (2006.01)
  *C07F 7/12* (2006.01)
  *G01N 33/92* (2006.01)
  *G01N 33/68* (2006.01)

(52) U.S. Cl.
  CPC ......... *G01N 33/57449* (2013.01); *C07F 7/12* (2013.01); *G01N 33/57442* (2013.01); *G01N 33/57488* (2013.01); *G01N 33/6872* (2013.01); *G01N 33/92* (2013.01); *G01N 2333/4703* (2013.01); *G01N 2333/4712* (2013.01); *G01N 2333/4727* (2013.01); *G01N 2405/04* (2013.01); *G01N 2610/00* (2013.01)

(58) Field of Classification Search
  CPC .............. C07F 7/12; G01N 2333/4703; G01N 2333/4712; G01N 2333/4727; G01N 2405/04; G01N 2610/00; G01N 33/57442; G01N 33/57449; G01N 33/57488; G01N 33/6872; G01N 33/92
  See application file for complete search history.

(56) References Cited

U.S. PATENT DOCUMENTS

| | | | |
|---|---|---|---|
| 6,248,553 B1 | 6/2001 | Small et al. | |
| 6,255,063 B1 | 7/2001 | Small et al. | |
| 7,964,408 B1 | 6/2011 | Sutphen | |
| 8,491,958 B2 | 7/2013 | Thompson et al. | |
| 2010/0291689 A1 | 11/2010 | Strongin et al. | |
| 2011/0306771 A1* | 12/2011 | Thompson | G01N 29/022 |
| | | | 548/110 |

FOREIGN PATENT DOCUMENTS

| | | |
|---|---|---|
| CA | 2389832 A1 | 5/2001 |
| WO | 2001032916 A2 | 5/2001 |
| WO | 2007109465 A2 | 9/2007 |
| WO | 2009029053 A1 | 3/2009 |
| WO | 2014144561 A2 | 9/2014 |

OTHER PUBLICATIONS

De La Franier et al., "Functionalizable self-assembled trichlorosilyl-based monolayer for application in biosensor technology," Appl. Surface Sci., 2017, vol. 414, pp. 435-441.*
Samanta et al., "Immobilization of bio-macromolecules on self-assembled monolayers: methods and sensor applications," Chem. Soc. Rev., 2011, vol. 40, pp. 2567-2592.*
Sheikh et al., "Single ether group in a glycol-based ultra-thin layer prevents surface fouling from undiluted serum," Chem. Commun., 2012, vol. 48, pp. 1305-1307.*
Vikhorev et al., "Bending Flexibility of Actin Filaments during Motor-Induced Sliding," Biophys J., 2008, vol. 95, No. 12, pp. 5809-5819.*
Bruce et al., "Surface Modification of Magnetic Nanoparticles with Alkoxysilanes and Their Application in Magnetic Bioseparations," Langmuir, 2005, vol. 21, No. 15, pp. 7029-7035.*
Kobayashi, E. et al., "Biomarkers for screening, diagnosis, and monitoring of ovarian cancer"; Cancer Epidemiol Biomarkers Prevention; (Published onlineFirst Sep. 7, 2012);1902-12.
Pages, C. et al., "Lysophosphatidic acid synthesis and release" Prostaglandins & Other Lipid Mediators 2001, 64, 1-10.
Xu, Y. et al., "Lysophosphatidic Acid as a Potential Biomarker for Ovarian and Other Gynecologic Cancers" JAMA 1998, 280(8), 719-723.
Sedlakova, I. et al., "Lysophosphatidic acid (LPA)—a perspective marker in ovarian cancer" Tumor Biol. 2011, 32(2), 311-316.
Meershaert, K. et al., "Gelsolin and functionally similar actin-binding proteins are regulated by lysophosphatidic acid" The EMBO Journal, 1998, 17(20), 5923-5932.
Shan, L. et al., "Quantitative determination of lysophosphatidic acid by LC/ESI/MS/MS employing a reversed phase HPLC column" J. Chromatogr. B, 2008, 864(1-2), 22-28.
Jesionowska et al., "Method for quantifying lysophosphatidic acid in body fluids: a review" Analytical Biochemistry 2014, 453, 38-43.

(Continued)

Primary Examiner — Galina M. Yakovleva
(74) Attorney, Agent, or Firm — Bereskin & Parr LLP/S.E.N.C.R.L., s.r.l.; Michael Fenwick

(57) ABSTRACT

The present disclosure relates to biosensors, kits and methods for detecting and/or quantifying lysophosphatidic acid (LPA) in a liquid sample such as a serum sample from a subject. The present disclosure also relates to linker compounds that are useful, for example, in the biosensors, kits and methods of the present disclosure and to methods for preparing a biosensor for detecting and/or quantifying lysophosphatidic acid (LPA) in a liquid sample.

16 Claims, 10 Drawing Sheets

(56) References Cited

OTHER PUBLICATIONS

Butanoyl chloride, 4-(trichlorosilyl)-; 62581-57-1; AGN-PC-OOP3HA . . . ; IUPAC name: 4-trichlorosilylbutanoyl chloride PubChem CID:15390371; Available online: https://pubchem.ncbi.nlm.nih.gov/compound/15390371, Feb. 9, 2007.
Undecanoyl Chloride, 11-(Trichlorosilyl)Undecanoyl Chloride; 17962-73-1; IUPAC name: 11-trichlorosilylundecanoyl chloride; PubChem CID: 71353360; Available online: https://pubchem.ncbi.nlm.nih.gov/compound/71353360, May 22, 2013.
Bearer. E. L., "Direct Observation of Actin Filament Severing by Gelsolin and Binding by gCap39 and CapZ", Journal of Cell Biology, 115 / 6, pp. 1629-1638, Dec. 6, 1991 (Jun. 12, 1991).

\* cited by examiner

BIOSENSORS AND METHODS FOR DETECTION OF LYSOPHOSPHATIDIC ACID FOR SIGNALING OF OVARIAN CANCER

CROSS-REFERENCE TO RELATED APPLICATIONS

The present application is a Divisional application which claims the benefit of priority to U.S. application Ser. No. 15/572,295 filed on Nov. 7, 2017, which claimed the benefit of priority to PCT/CA2016/050545, filed May 13, 2016, which claimed the benefit of priority to U.S. Provisional Application No. 62/160,800, filed on May 13, 2015, the contents of which are incorporated herein by reference in their entirety.

FIELD

The present disclosure relates to biosensors, kits and methods for detecting and/or quantifying lysophosphatidic acid (LPA) in a liquid sample such as a serum sample from a subject. The present disclosure also relates to linker compounds that are useful, for example, in the biosensors, kits and methods of the present disclosure and to methods for preparing a biosensor for detecting and/or quantifying lysophosphatidic acid (LPA) in a liquid sample.

BACKGROUND

In women over 50, cancer is one of the leading causes of death, at 15%, making it a serious problem around the world.[1] Among female cancers, one of the most dangerous is ovarian cancer. Ovarian cancer is a general term used to identify any cancers that originate or find their main tumors in an ovary.[2] Though ovarian cancer is less common than other female cancers, such as breast cancer, it has the highest fatality to case ratio of all gynecological cancers making it a serious issue especially for post-menopausal women.[3]

Ovarian cancer accounts for over 225,000 new cases and over 140,000 deaths worldwide each year.3 Though the majority of ovarian cancer cases are diagnosed in older women, the disease is also present in younger populations, with girls in their teens being diagnosed and even dying of the disease each year.[4] Despite increased survival rates for other cancers over the last few decades, the survival rate for ovarian cancer has remained roughly steady since 1995, with a 5 year survival rate of less than 40% of those women who survive their first year.[5] Survival rates for the disease have improved little since the 1970s despite advances in cancer treatment and surgery.[6]

At more than 70%, the majority of women are diagnosed with late stage ovarian cancer. Unfortunately, the five year survival rate for women diagnosed at a late stage, versus those diagnosed in stages I or II, is extremely low with less than 40% of late stage women surviving 5 years compared to 90% for those diagnosed in early stages.4 This decreased survival rate is mostly due to the unusually rapid rate of ovarian cancer metastasis, which is due to a lack of anatomical barrier to prevent seeding of the tumor into the peritoneal cavity.2 As a result, it may be useful to improve diagnosis in the early stages of the disease to increase the survival rate for those women who suffer from it.

Ovarian cancer often presents with few symptoms at an early stage and vague symptoms at later stages. These symptoms include, for example, bloating, nausea, difficulty eating, back pain and urinary urgency among others, which tend to persist and worsen as the cancer advances.[7] Because these symptoms don't tend to appear until the later stages of the disease, early detection may, for example, be more difficult as women with the disease may, for example, have little to no physical indication of its presence.

Ovarian cancer typically presents as adnexal masses, which are relatively common and rarely malignant.[8] In approximately 1% of women who have these adnexal masses, the adnexal masses do turn out to be malignant, and for the remaining majority it is useful to avoid unnecessary interventions.[9] As such, it may, for example, be useful to establish the nature of these masses by imaging techniques before proceeding with biopsies and further testing.

The most common technique for imaging ovarian masses is transvaginal ultrasonography (TVU), which allows for basic imaging of the masses. Early stage and benign masses share different physical characteristics to later stage and malignant masses, which can be seen by TVU. These characteristics of late stage tumors include, for example, more papillary projections, more commonly being multilocus, larger in size, and containing more solid mass than early stage tumors.[10]

Differences also exist between benign and malignant masses when imaged by magnetic resonance imaging. Due to the presence of solid and cystic areas within malignant masses, as well as necrosis within the solid tissue, they appear to be hyperintense on diffusion-weighted images, with only intermediate intensity on T2-weighted images, whereas benign masses tend to be hypointense on both of these images.8

Currently there is no viable blood-based detection method in use for the disease to indicate if a woman is in need of further imaging studies. One biomarker for the disease currently being tested for is cancer antigen 125 (CA-125). CA-125 has been used to monitor ovarian cancer patients for over three decades, but is not viable on its own for the detection of ovarian cancer. This is because it is only present at elevated levels in approximately half of patients at an early stage, and 92% of late stage patients. So, on its own, it can't be used to identify most early stage ovarian cancer patients when detection is most useful, and it isn't applicable for monitoring of all patients, as 8% of late stage patients and approximately 50% of early stage patients won't show elevated levels. It is also present at elevated levels in benign conditions such as pregnancy or menstruation giving it a high rate of false positives when used for detection.[11]

Lysophosphatidic acid (LPA) is a signaling lipid.[12] In two separate studies, this signaling lipid was found to be elevated in 90% of stage I ovarian cancer patients, and 100% of later stage patients.[13,14] It was also found that LPA elevation correlated to the stage of the disease with stage III and IV patients presenting higher LPA serum concentrations than stage I and II patients.[14] However, as with the CA-125 biomarker discussed above, LPA levels were found to be elevated in a subset of healthy controls and patients with benign gynecological diseases, approximately 10% and 25% respectively.[13]

SUMMARY

The ability to detect and quantify lysophosphatidic acid (LPA) by a test comprising ultraviolet-visible (UV-visible or UV-vis) absorbance spectroscopy or fluorescence spectroscopy and which used gelsolin and modified actin proteins as a dual probe system has been disclosed herein. This test may, for example, be useful in the early detection of ovarian cancer, as LPA is a biomarker for the disease that is present in most patients at all stages of the cancer. The test has been found to show promise in reproducibility and long-term storage. In the studies disclosed herein, mixed, self-assembling monolayers (SAMs) containing linker components and diluent components were assembled on a solid support (a plastic surface or a silica gel), then protein probes were subsequently immobilized onto the linkers in a straightforward manner. Absorbance spectroscopy (UV-vis) or fluorescence was used to test solutions comprising LPA that were subjected to the biosensors thereby produced. These SAM-modified biosensors may, for example, be useful for detection and/or quantification of LPA in a method that is rapid and label-free. The linkers described herein bind to the protein probes with no detected release of the probe during testing.

Accordingly, the present disclosure includes a biosensor for detecting and/or quantifying lysophosphatidic acid (LPA) in a liquid sample, the biosensor comprising:

(a) a solid support; and
(b) a dual protein system comprising gelsolin and dye-modified actin, wherein
the actin is bound to an actin-binding site of the gelsolin; and
the gelsolin is bound to the solid support.

In an embodiment of the present disclosure, the biosensor is bound to the solid support via a linker.

In another embodiment, the linker has the following structure:

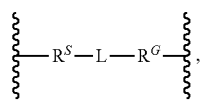

wherein
$R^S$ is a functional group covalently bonded to the solid support;
$R^G$ is a functional group covalently bonded to the gelsolin; and
L is $C_{2-20}$ alkylene, wherein one or more available carbon atoms in the alkylene are optionally replaced by —O— or —S—.

In an embodiment, L is —(CH$_2$)$_2$—O—(CH$_2$)$_2$—.

In an embodiment, the gelsolin comprises a histidine tag and $R^G$ is bonded to the histidine tag of the gelsolin. In another embodiment, $R^G$ comprises a Ni-NTA moiety that is bonded to the histidine tag of the gelsolin. In a further embodiment, the Ni-NTA moiety comprises an NTA moiety of the following structure that is coordinated to a Ni$^{2+}$ ion:

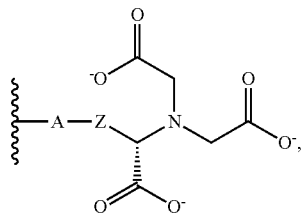

wherein
A is —C(O)NH—, —NHC(O)—, —C(O)O—, —OC(O)— or —O—; and
Z is $C_{2-14}$alkylene, wherein one or more available carbon atoms in the alkylene are optionally replaced by —O— or —S—.

In another embodiment, the Ni-NTA moiety comprises an NTA moiety of the following structure that is coordinated to a Ni$^{2+}$ ion:

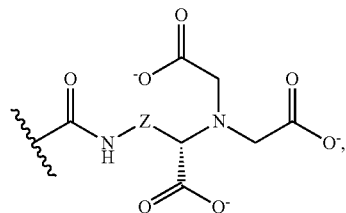

wherein
Z is $C_{2-14}$alkylene or —(CH$_2$CH$_2$—O—)$_m$CH$_2$CH$_2$; and
m is 1, 2 or 3.

In an embodiment, $R^S$ comprises a silicon atom and the linker is bound to the solid support via a silicon-oxygen bond.

In an embodiment, the linker is comprised in a self-assembled monolayer (SAM) that is on a surface of the solid support.

In an embodiment, the SAM comprises a siloxane network comprising linkers of the following structure:

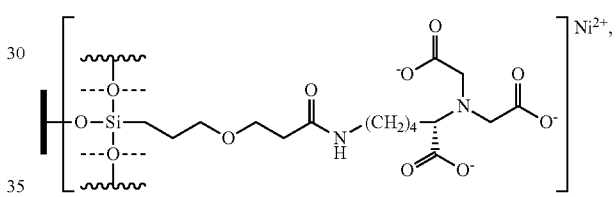

wherein
▬ represents the surface of the solid support; and
each ⊙ represents an oxygen atom in the siloxane network.

In another embodiment, the SAM further comprises a diluent.

In another embodiment, the SAM is a mixed SAM and the siloxane network further comprises diluents of the following structure:

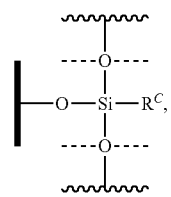

wherein
$R^C$ is selected from:
(i) $C_{1-24}$alkyl, wherein one or more available carbon atoms in the alkyl are optionally replaced by —O— or —S—;
(ii) $C_{1-24}$alkylene-O—C(O)CF$_3$, wherein one or more available carbon atoms in the alkylene are optionally replaced by —O— or —S—; and
(iii) $C_{1-24}$alkylene-OH, wherein one or more available carbon atoms in the alkylene are optionally replaced by —O— or —S—;

■ represents the surface of the solid support; and each --O-- represents an oxygen atom in the siloxane network.

In a further embodiment, $R^C$ is hexyl, octadecyl or 3-(2-(2,2,2-trifluoroacetoxy)ethoxy)propyl, optionally wherein $R^C$ is hexyl.

In another embodiment, the dye-modified actin is rhodamine-modified actin. In a further embodiment, the dye-modified actin is N-hydroxysuccinimide(NHS)-rhodamine-modified actin.

In an embodiment, the solid support comprises plastic, glass, metal, metal oxide or crystal or the solid support comprises silica gel or magnetic nanoparticles. In another embodiment, the solid support consists essentially of silica gel.

In an embodiment, when the solid support comprises plastic, glass, metal, metal oxide or crystal, the solid support is in the form of a testing strip, a well in a microwell plate or a microcentrifuge tube. In another embodiment, the solid support is in the form of a microcentrifuge tube. In another embodiment, when the solid support comprises or consists essentially of silica gel or comprises magnetic nanoparticles, the silica gel or magnetic nanoparticles are housed in a column, vial or tube.

In an embodiment, the biosensor is for use in diagnosing a risk of ovarian cancer in a subject which can then be confirmed.

The present disclosure also includes a kit for detecting and/or quantifying lysophosphatidic acid (LPA) in a liquid sample, the kit comprising:

(a) a biosensor for detecting and/or quantifying lysophosphatidic acid (LPA) in a liquid sample of the present disclosure; and (b) optionally instructions for use.

In an embodiment, the solid support of the biosensor is in the form of a testing strip, a well in a microwell plate or a microcentrifuge tube or the solid support consists essentially of silica gel or magnetic nanoparticles housed in a column, vial or tube, and:

(a) when the solid support is in the form of a testing strip, the kit further comprises one control testing strip per each 2 or 3 biosensors in the kit, the control testing strip made of the same solid support as the biosensors but not the dual protein system or linker;

(b) when the solid support is in the form of a well in a microwell plate, the microwell plate comprises one control well per each 2 or 3 biosensors in the microwell plate, the control well made of the same solid support as the biosensors but not the dual protein system or linker;

(c) when the solid support is in the form of a microcentrifuge tube, the kit further comprises one control tube per each 2 or 3 biosensors in the kit, the control tube made of the same solid support as the biosensors but not the dual protein system or linker; and (d) when the solid support consists essentially of silica gel or magnetic nanoparticles housed in a column, vial or tube, the kit further comprises one control column, vial or tube per each 2 or 3 biosensors in the kit, the control column, vial or tube containing the same solid support as the biosensors but not the dual protein system or linker.

In an embodiment, the kit further comprises a predetermined amount of LPA.

In another embodiment, the kit is for use in diagnosing a risk of ovarian cancer in a subject which can then be confirmed.

The present disclosure also includes a method for detecting lysophosphatidic acid (LPA) in a liquid sample, the method comprising:

exposing the sample to a biosensor of the present disclosure under conditions to bind the LPA to the gelsolin and thereby release the dye-modified actin into the liquid; and analyzing the sample after exposure to the biosensor to determine if LPA was present in the liquid sample, wherein the step of analyzing comprises spectroscopically measuring a signal associated with the dye of the dye-modified actin.

In an embodiment, the method quantifies the amount of LPA in a liquid sample, and comprises:

exposing a first portion of the sample to a first biosensor;

analyzing the first portion of the sample after exposure to the first biosensor to obtain a first signal value;

adding a known amount of LPA to a second portion of the sample;

exposing the second portion of the sample to a second biosensor; analyzing the second portion of the sample after exposure to the second biosensor to obtain a second signal value;

exposing a third portion of the sample to a control made of the same solid support as the biosensors but not the dual protein system or linker;

analyzing the third portion of the sample after exposure to the control to obtain a control signal value; and calculating the ratio of the first signal value minus the control signal value to the second signal value minus the control signal value to determine the concentration of LPA that was present in the sample, wherein the first biosensor and the second biosensor are each made of the same solid support, dual protein system and linker; and wherein the steps of analyzing comprise spectroscopically measuring a signal associated with the dye of the dye-modified actin.

In an embodiment, the solid support of each biosensor and the control is in the form of a testing strip, a well in a microwell plate, silica gel or magnetic nanoparticles. In another embodiment, the solid support of each biosensor and the control is in the form of silica gel housed in a column, vial or tube.

In another embodiment, the method quantifies the amount of LPA in a liquid sample, and comprises:

exposing a first portion of the sample to a first biosensor;

analyzing the first portion of the sample after exposure to the first biosensor to obtain a first signal value;

adding different known amounts of LPA to each of a plurality of additional portions of the sample;

exposing each of the plurality of additional portions of the sample to a respective plurality of additional biosensors;

analyzing each of the plurality of additional portions of the sample after exposure to the respective plurality of additional biosensors to obtain a plurality of additional signal values;

plotting the signal value obtained for each portion of the sample against the corresponding concentration of LPA added to the portion of the sample; and obtaining the concentration of LPA that was present in the sample from the y-intercept of the line of best fit for the plot, wherein the steps of analyzing comprise spectroscopically measuring a signal associated with the dye of the dye-modified actin.

In an embodiment, the solid support of each biosensor is in the form of a testing strip, a well in a microwell plate, silica gel or magnetic nanoparticles. In another embodiment, the solid support of each biosensor is in the form of silica gel housed in a column, vial or tube.

In an embodiment of the present disclosure, the analyzing comprises the use of a robotic system.

In an embodiment, each sample or the portion thereof, as applicable, is exposed to the biosensor for a time of at least about 10 seconds, optionally, for a time of about 10 seconds to about 25 minutes. In another embodiment, each sample or the portion thereof, as applicable, is exposed to the biosensor for a time of about 10 seconds to about 10 minutes.

In an embodiment, the actin is modified with a dye suitable for detection by UV-visible absorbance spectroscopy and the step(s) of analyzing comprise(s) measuring, by ultraviolet-visible absorbance spectroscopy, a signal associated with said dye. In another embodiment, the dye-modified actin is rhodamine-modified actin and the method comprises measuring the signal at a wavelength of about 500 nm to about 590 nm. In a further embodiment, the dye-modified actin is N-hydroxysuccinimide(NHS)-rhodamine-modified actin and the method comprises measuring the signal at a wavelength of about 540 nm to about 560 nm, optionally measuring the signal at a wavelength of about 552 nm.

In another embodiment, the actin is modified with a dye suitable for detection by fluorescence spectroscopy and the step(s) of analyzing comprise(s) measuring, by fluorescence spectroscopy, a signal associated with said dye. In a further embodiment, the dye-modified actin is rhodamine-modified actin and the method comprises irradiating the sample at a wavelength of about 500 nm to about 590 nm, and measuring the resulting fluorescence signal at a wavelength of about 530 nm to about 620 nm, optionally wherein the dye-modified actin is N-hydroxysuccinimide(NHS)-rhodamine-modified actin and the method comprises irradiating the sample at a wavelength of about 540 nm to about 560 nm, optionally irradiating the sample at a wavelength of about 552 nm, followed by measuring the resulting fluorescence signal at a wavelength of about 560 nm to about 595 nm, optionally measuring the fluorescence signal at a wavelength of about 572 nm.

In another embodiment, the liquid sample is a serum sample from a subject, optionally wherein the subject is a woman over the age of fifty and/or wherein the woman has a family history of ovarian cancer.

In another embodiment, the concentration of LPA in the serum sample is determined to be above about 1.5 µM and the method further comprises determining whether or not the subject has ovarian cancer by a method which comprises using an imaging technique, optionally wherein the imaging technique comprises transvaginal ultrasound (TVU).

The present disclosure also includes a compound of Formula I:

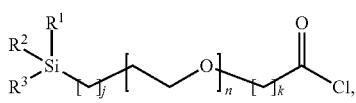

(I)

wherein
$R^1$, $R^2$ and $R^3$ are each independently a hydrolysable group that does not react with an acid chloride;
j is 0, 1, 2 or 3;
k is 2, 3, 4 or 5; and
n is 1, 2, 3, 4 or 5.

In an embodiment, j is 0 and k is 2. In another embodiment, $R^1$, $R^2$ and $R^3$ are all chloro. In a further embodiment, n is 1.

The present disclosure also includes a method for preparing a biosensor for detecting and/or quantifying lysophosphatidic acid (LPA) in a liquid sample, the method comprising:
(a) reacting a solid support having hydroxyl groups on its surface with a compound of Formula I of the present disclosure under conditions to hydrolyze the hydrolysable groups and thereby form a self-assembled monolayer (SAM) comprising a siloxane network bound to the surface of the solid support;
(b) reacting the product obtained from (a) with an NTA moiety of the Formula II under conditions so that the acid chloride from the compound of Formula I and the amine from the compound of Formula II react to form an amide linkage:

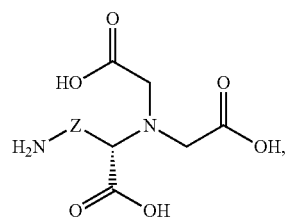

(II)

wherein
Z is $C_{2-14}$alkylene or $-(CH_2CH_2-O-)_mCH_2CH_2$; and
m is 1, 2 or 3;
(c) reacting the product obtained from (b) with a nickel (II) compound under conditions to form a complex between the $Ni^{2+}$ and the carboxylate groups from the compound of Formula II;
(d) reacting the product obtained from (c) with his-tagged gelsolin under conditions to bind the Ni-NTA moiety to the his-tag; and
(e) reacting the product obtained from (d) with dye-modified actin under conditions to bind the actin to the gelsolin.

In an embodiment, the compound of Formula I is 3-(3-(trichlorosilyl)propoxy)propanoyl chloride. In another embodiment, the compound of Formula II is Nα,N-bis (carboxymethyl)-L-lysine hydrate (ab-NTA).

In an embodiment, the nickel (II) compound is $NiCl_2$.

In an embodiment, the dye-modified actin is rhodamine-modified actin. In another embodiment, the dye-modified actin is N-hydroxysuccinimide(NHS)-rhodamine-modified actin.

In an embodiment, the method further comprises, in (a), reacting the solid support having hydroxyl groups on its surface with a diluent compound of Formula III under conditions to hydrolyze the hydrolysable groups and thereby form a mixed, self-assembled monolayer (SAM) comprising a siloxane network that is bound to the surface of the solid support:

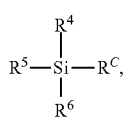

(III)

wherein $R^4$, $R^5$ and $R^6$ are each independently a hydrolysable group that does not react with an acid chloride; and $R^C$ is is selected from:
(i) $C_{1-24}$alkyl, wherein one or more available carbon atoms in the alkyl are optionally replaced by —O— or —S—;
(ii) $C_{1-24}$alkylene-O—C(O)CF$_3$, wherein one or more available carbon atoms in the alkylene are optionally replaced by —O— or —S—; and
(iii) $C_{1-24}$alkylene-OH, wherein one or more available carbon atoms in the alkylene are optionally replaced by —O— or —S—.

In an embodiment, $R^C$ is hexyl, octadecyl or 3-(2-(2,2,2-trifluoroacetoxy)ethoxy)propyl, optionally wherein $R^C$ is hexyl. In another embodiment, $R^4$, $R^5$ and $R^6$ are all chloro.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings in which.

DETAILED DESCRIPTION

I. Definitions

Figure 1:
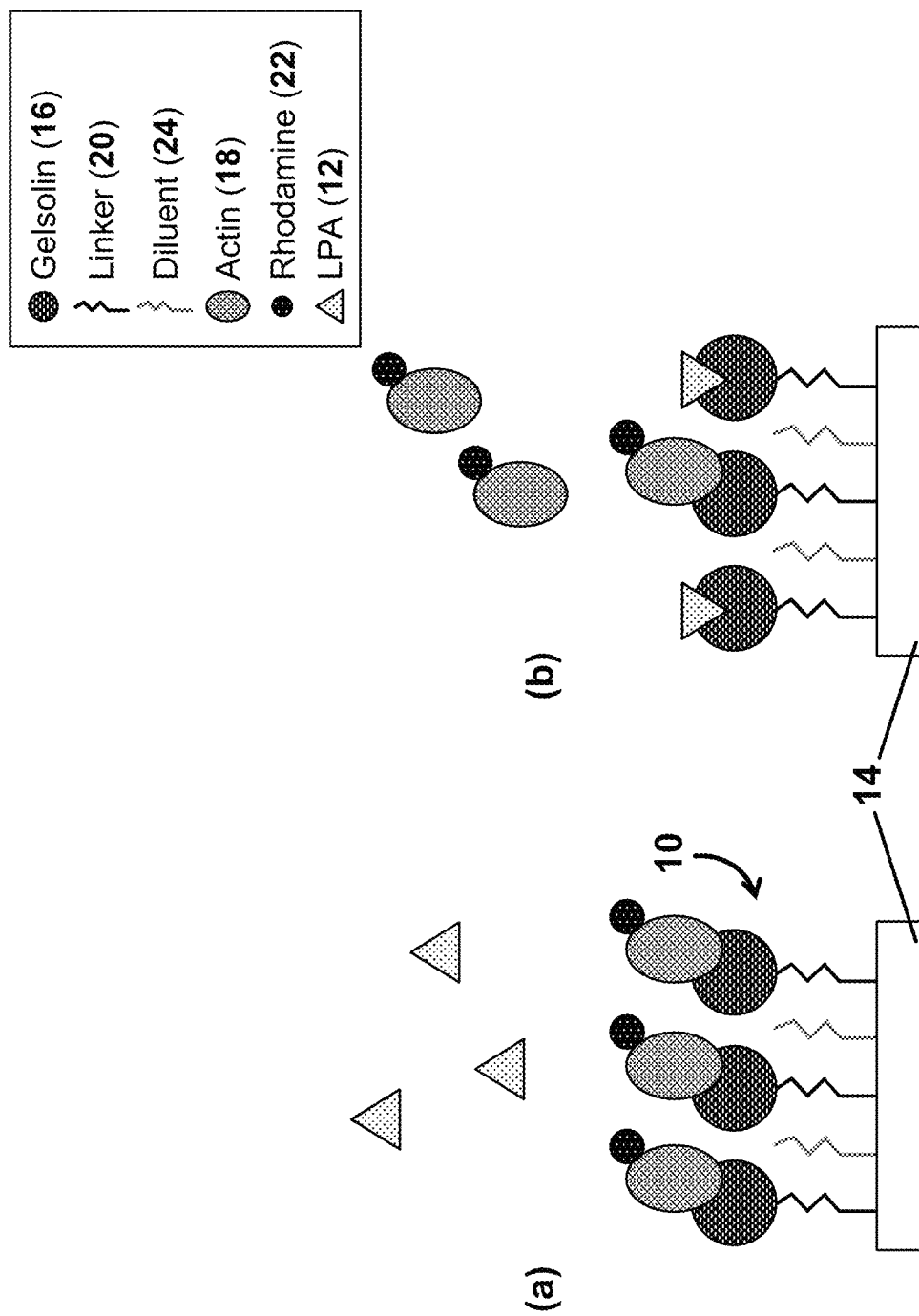
FIG. 1 is a schematic representation of an embodiment of a biosensor for detecting and/or quantifying LPA of the present disclosure.

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in the present disclosure, the singular forms "a", "an" and "the" include plural references unless the content clearly dictates otherwise. For example, an embodiment including "a biosensor" should be understood to present certain aspects with one biosensor or two or more additional biosensors.

In embodiments comprising an "additional" or "second" component, such as an additional or second biosensor, the second component as used herein is different from the other components or first component. A "third" component is different from the other, first, and second components, and further enumerated or "additional" components are similarly different.

The term "suitable" as used herein means that the selection of specific reagents or conditions will depend on the reaction being performed and the desired results, but none-the-less, can generally be made by a person skilled in the art once all relevant information is known.

The term "available", as in "available carbon atoms" refers to carbon atoms that would be known to a person skilled in the art to be capable of replacement by an oxygen atom or a sulfur atom using methods known in the art.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1\text{-}n2}$". For example, the term $C_{1\text{-}24}$alkyl means an alkyl group having 1, 2, 3, 4, 5, 6, 7, 8, 9, 10, 11, 12, 13, 14, 15, 16, 17, 18, 19, 20, 21, 22, 23 or 24 carbon atoms.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1\text{-}n2}$". For example, the term $C_{2\text{-}14}$alkylene means an alkylene group having 2, 3, 4, 5, 6, 7, 8, 9, 10, 11, 12, 13 or 14 carbon atoms.

The term "gelsolin" as used herein refers, for example, to gelsolin from any species or source and includes the full-length protein as well as isoforms, analogs, variants, functional derivatives, fragments or portions of the protein so long as the full-length protein or isoform, analog, variant, functional derivative, fragment or portion thereof is capable of binding dye-modified actin at an actin-binding site and so long as lysophosphatidic acid (LPA) is capable of binding to the full-length protein or isoform, analog, variant, functional derivative, fragment or portion thereof under conditions to release the dye-modified actin into a liquid sample. It will be appreciated by a person skilled in the art that gelsolin is an actin-binding protein that is a regulator of actin filament assembly and disassembly. The selection of a suitable gelsolin can be made by a person skilled in the art. In an embodiment, the gelsolin is human gelsolin. For example, a Genbank Accession number of human plasma gelsolin is CAA28000.

The term "actin" as used herein refers, for example, to actin from any species or source and includes the full-length protein as well as isoforms, analogs, variants, functional derivatives, fragments or portions of the protein so long as the full-length protein or isoform, analog, variant, functional derivative, fragment or portion thereof is capable of binding to an actin-binding site of gelsolin and so long as lysophosphatidic acid (LPA) is capable of binding to the gelsolin under conditions to release the full-length protein or isoform, analog, variant, functional derivative, fragment or portion thereof into a liquid sample. It will be appreciated by a person skilled in the art that there is little variation of actin between species. The selection of a suitable actin can be made by a person skilled in the art. In an embodiment, the actin is from rabbit muscle.

The term "isoform" as used herein refers to a protein that contains the same number and kinds of amino acids as a protein disclosed herein, but the isoform has a different molecular structure. The isoforms contemplated by the present disclosure are those having the same properties as the corresponding protein described herein.

The term "analog" as used herein refers to a protein that has been modified as compared to the sequence of a protein described herein. Modifications may include, but are not limited to, amino acid substitutions, insertions, and/or deletions. The amino acid substitutions may be of a conserved or non-conserved nature. Analogs of a protein disclosed herein may be prepared by introducing mutations in the nucleotide sequence encoding the protein.

The term "variant" as used herein includes modifications, substitutions, additions, or chemical equivalents of the amino acid sequence of a protein disclosed herein that perform substantially the same function as the protein disclosed herein in substantially the same way. For example, a variant of a protein disclosed herein includes, without limitation, conservative amino acid substitutions. Variants of polypeptides also include additions and deletions to the polypeptide sequences disclosed herein.

The term "conservative amino acid substitution" as used herein refers to replacing one or more amino acids of a protein disclosed herein with amino acids of similar charge, size, and/or hydrophobicity characteristics. Conservative substitutions are described in the patent literature, as for example, in U.S. Pat. No. 5,264,558. When only conserved substitutions are made, the resulting protein should be functionally equivalent. Non-conserved substitutions involve replacing one or more amino acids of the amino acid sequence with one or more amino acids which possess dissimilar charge, size, and/or hydrophobicity characteristics.

The term "rhodamine" as used herein, refers to a dye from a family of fluorone dyes based on the following core structure:

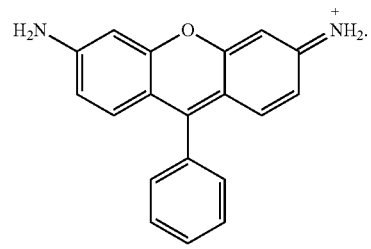

Various dyes that are derivatives of rhodamine are known. For example, the term "N-hydroxysuccinimide-rhodamine" or "NHS-rhodamine" and the like as used herein refers to a rhodamine dye having the following structure:

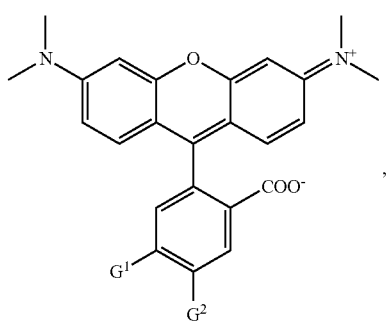

wherein
one of $G^1$ and $G^2$ is H; and
the other of $G^1$ and $G^2$ is

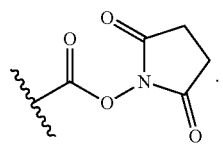 [SMILES: *C(=O)ON1C(=O)CCC1=O]

For example, NHS-rhodamine is commercially available as a combination of 5-carboxytetramethylrhodamine, succinimidyl ester and 6-carboxytetramethylrhodamine, succinimidyl ester.

II. Biosensors and Kits

In the studies of the present disclosure, two types of methods for detecting lysophosphatidic acid (LPA) in a liquid sample using a biosensor were investigated; one based on UV-visible absorbance spectroscopy and the other based on fluorescence spectroscopy. Biosensors were prepared in which a protein probe was bound to the surface of a solid support (a plastic strip or silica gel) by a linker in a mixed self-assembled monolayer comprising the linker moieties and diluent moieties. The diluent was prepared starting from octadecyltrichlorosilane (OTS) or hexyltrichlorosilane. The linker was prepared starting from 3-(3-(trichlorosilyl)propoxy)propanoyl chloride (Meg-Cl) which, after being bound to the solid support was subsequently reacted with Nα,Nα-bis(carboxymethyl)-L-lysine hydrate (ab-NTA) to form an amide linkage. After treating the NTA-functionalized surface with nickel (II) chloride, the surface was functionalized with a his-tagged version of the human protein gelsolin. Actin which had been modified with N-hydroxysuccinimide(NHS)-rhodamine was then immobilized on the gelsolin. The biosensors so-prepared were used in a method of detecting lysophosphatidic acid (LPA) comprising UV-visible absorbance spectroscopy or fluorescence spectroscopy to detect the absorbance or emission, respectively, of actin released from the gelsolin upon binding of the LPA to the gelsolin. The concentration of LPA in a sample can be quantified, for example, by relating absorbance or emission, respectively, of the sample to a calibration curve prepared using samples with known concentrations of LPA. Biosensors were shown to be useful in such a method for detecting LPA, for example, after 28 days of storage in buffer at 4° C. and after 42 days of storage at 4° C. in atmosphere.

An exemplary schematic of an embodiment of a biosensor of the present disclosure is shown in FIG. 1. The exemplified biosensor 10 is for detecting and/or quantifying lysophosphatidic acid (LPA) in a liquid sample. FIG. 1(a) depicts a liquid sample comprising LPA 12 being exposed to the biosensor 10. The biosensor comprises a solid support 14; a dual protein system comprising gelsolin 16 and dye-modified actin 18; and a linker 20 binding the gelsolin 16 to the solid support 14. The dye-modified actin 18 is bound to an actin-binding site of the gelsolin 16. In the embodiment shown in FIG. 1, the dye-modified actin 18 is actin that has been modified with NHS-rhodamine 22, the linker 20 is comprised in a self-assembled monolayer (SAM) that is on a surface of the solid support 14 and the SAM further comprises a diluent 24. FIG. 1(b) depicts that on exposure to the biosensor 10, LPA 12 in the sample binds with gelsolin 16 which releases the dye-modified actin 18 into the liquid. In the methods for detecting and/or quantifying LPA of the present disclosure, a signal associated with the dye-modified actin can then be spectroscopically measured. For example, in methods comprising the biosensor of the embodiment shown in FIG. 1, a signal at a wavelength of 552 nm associated with the NHS-rhodamine dye can be measured using an ultraviolet-visible absorbance spectrometer or an emission wavelength of 572 nm can be measured using a fluorescence spectrometer when an excitation wavelength of 552 nm is used.

Accordingly, the present disclosure includes a biosensor for detecting and/or quantifying lysophosphatidic acid (LPA) in a liquid sample, the biosensor comprising:
(a) a solid support; and
(b) a dual protein system comprising gelsolin and dye-modified actin, wherein
the actin is bound to an actin-binding site of the gelsolin; and
the gelsolin is bound to the solid support.

The actin is bound to an actin-binding site of the gelsolin through a reversible non-covalent binding that can be released by LPA. It will be appreciated by a person skilled in the art that there are multiple sites on gelsolin that can bind actin, but each gelsolin will bind one or two actin molecules[16].

Gelsolin can be bound to the solid support by any suitable means. It will be appreciated by a person skilled in the art that gelsolin may even, for example, be bound directly to the solid support, for example, through fouling interactions. However, the use of a linker to bind the gelsolin to the solid support may, for example, provide certain benefits over a system where the gelsolin is directly bound to the solid support. For example, there may be a more stable connection between the gelsolin and the solid support and/or there may be less error between runs of a method that uses such biosensors to detect and/or quantify LPA in a liquid sample. Accordingly, in an embodiment of the present disclosure, the gelsolin is bound to the solid support via a linker.

In another embodiment, the biosensor comprises:
(a) a solid support;
(b) a dual protein system comprising gelsolin and dye-modified actin, wherein the dye-modified actin is bound to an actin-binding site of the gelsolin; and
(c) a linker binding the gelsolin to the solid support.

The linker can be any suitable linker and can bind the gelsolin to the solid support in a covalent or a non-covalent manner. In an embodiment, the linker binds the gelsolin to the solid support via a covalent bond.

In another embodiment, the linker has the following structure:

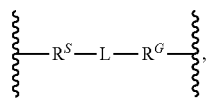

wherein $R^S$ is a functional group covalently bonded to the solid support;

$R^G$ is a functional group covalently bonded to the gelsolin; and

L is $C_{2-20}$alkylene, wherein one or more available carbon atoms in the alkylene are optionally replaced by —O— or —S—.

$R^S$ can be any functional group suitable to covalently bond to the solid support, the selection of which can be made by a person skilled in the art. For example, functional groups comprising a sulfur atom may be used, for example, to bind to a surface comprising gold. Other functional groups may be used for different surfaces. For example, a functional group comprising a secondary amine may be used to bind to surfaces comprising an acid halide functionality, a carboxylic acid functionality or a mixture thereof and a functional group comprising an ester may be used to bind to surfaces comprising an alcohol functionality, an amine functionality or a mixture thereof. A functional group comprising a silicon atom wherein the linker is bound to the solid support via a silicon-oxygen bond may, for example, be derived from a precursor comprising a trichlorosilane moiety. Such a precursor may, for example, bind to a variety of different surfaces. Accordingly, in an embodiment, $R^S$ comprises a silicon atom and the linker is bound to the solid support via a silicon-oxygen bond.

$R^G$ can be any functional group suitable to covalently bond to the gelsolin. For example, in an embodiment, the gelsolin comprises a lysine group at the C-terminal and $R^G$ is bonded to the C-terminal lysine group of the gelsolin. For example, gelsolin is prepared which comprises a lysine group at the C-terminal before a histidine tag, the histidine tag is removed after purification and $R^G$ comprises a —C(O)— functional group (optionally derived from an acid chloride) bonded to the NH of the C-terminal lysine. In an alternative embodiment, the gelsolin comprises a histidine tag and $R^G$ is bonded to the histidine tag of the gelsolin. Such systems, may, for example, be easier and less expensive to implement than systems comprising a lysine group at the C-terminal. In another embodiment, $R^G$ comprises a Ni-NTA moiety (i.e. a moiety comprising $Ni^{2+}$ which is coordinated to a moiety comprising nitrilotriacetic acid; NTA).

In a further embodiment, the Ni-NTA moiety comprises an NTA moiety of the following structure that is coordinated to a $Ni^{2+}$ ion:

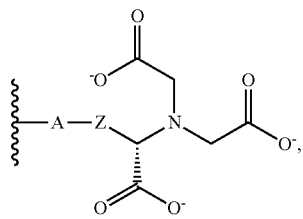

wherein

A is —C(O)NH—, —NHC(O)—, —C(O)O—, —OC(O)— or —O—; and

Z is $C_{2-14}$alkylene, wherein one or more available carbon atoms in the alkylene are optionally replaced by —O— or —S—.

When A comprises —C(O)NH—, this moiety can be readily prepared from the reaction of an acid chloride with, for example, ab-NTA. Accordingly, in a further embodiment of the present disclosure, the Ni-NTA moiety comprises an NTA moiety of the following structure that is coordinated to a $Ni^{2+}$ ion:

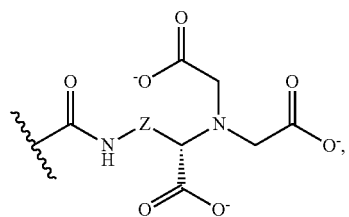

wherein

Z is $C_{2-14}$alkylene or —$(CH_2CH_2$—O—$)_mCH_2CH_2$; and m is 1, 2 or 3.

In an embodiment, Z is $C_{2-14}$alkylene. In another embodiment, Z is $C_{2-6}$alkylene. In a further embodiment of the present disclosure, Z is —$(CH_2)_4$—.

In an embodiment, Z is $C_{2-14}$alkylene, wherein one or more available carbon atoms in the alkylene are optionally replaced by —O—. In another embodiment, Z is —$(CH_2CH_2$—O—$)_mCH_2CH_2$. In a further embodiment, m is 1.

In an embodiment, L is $C_{2-20}$alkylene. In another embodiment, L is $C_{3-7}$alkylene. In a further embodiment of the present disclosure, L is —$(CH_2)_5$—.

In an embodiment, L is $C_{2-20}$alkylene, wherein one or more available carbon atoms in the alkylene are optionally replaced by —O—. In another embodiment, L is —$(CH_2CH_2$—O$)_n$—$CH_2CH_2$—, wherein n is 1, 2, 3, 4, 5 or 6. In another embodiment of the present disclosure, L is —$(CH_2CH_2$—O$)_n$—$CH_2CH_2$—, wherein n is 1, 2, 3, 4 or 5. In a further embodiment, L is —$(CH_2CH_2$—O$)_n$—$CH_2CH_2$—, wherein n is 1, 2, 3 or 4. It is an embodiment that L is —$(CH_2CH_2$—O$)_n$—$CH_2CH_2$—, wherein n is 1, 2 or 3. In another embodiment, L is —$(CH_2CH_2$—O$)_n$—$CH_2CH_2$—, wherein n is 1 or 2. In a further embodiment, L is —$(CH_2)_2$—O—$(CH_2)_2$—.

In an embodiment, the linker is comprised in a self-assembled monolayer (SAM) that is on a surface of the solid support.

In a further embodiment, the SAM further comprises a diluent (i.e. a moiety which is attached to the solid support which does not bind to the gelsolin). SAMs comprising both a linker and a diluent are optionally referred to herein as a "mixed self-assembled monolayer" or a "mixed SAM" and the like. The diluent can be any suitable diluent. In an embodiment, the linker and diluent are present in the SAM in a molar ratio of about 5:1 to about 1:5. In another embodiment, the linker and diluent are present in the SAM in a molar ratio of about 1:1. In an embodiment, the SAM comprises a siloxane network binding the linker to the solid support; i.e. $R^S$ comprises a silicon atom, the linker is bound to the solid support via one silicon-oxygen bond; the linker is bound to another linker or to a diluent, as the case may be, through a second silicon-oxygen bond; and the linker is bound to further linker or to a diluent, as the case may be, through a third silicon-oxygen bond, thereby forming a siloxane network which is bound to the solid support. It will be appreciated that the exact structure of the siloxane network will vary, for example, depending on the conditions used. For example, a person skilled in the art would understand that not all of the hydrolysable groups in a precursor to the siloxane network may participate in a condensation reaction so that the siloxane network may comprise variable amounts of silanol (i.e. Si—OH) endgroups.

In an embodiment, the SAM comprises a siloxane network comprising linkers of the following structure:

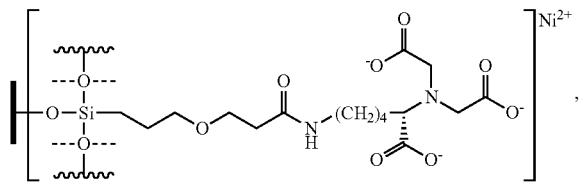

wherein
▬▬▬▬ represents the surface of the solid support; and
each --O-- represents an oxygen atom in the siloxane network.

In another embodiment, the SAM is a mixed SAM and the siloxane network further comprises diluents of the following structure:

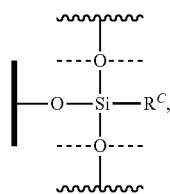

wherein
$R^C$ is selected from:
(i) $C_{1-24}$alkyl, wherein one or more available carbon atoms in the alkyl are optionally replaced by —O— or —S—;
(ii) $C_{1-24}$alkylene-O—C(O)CF$_3$, wherein one or more available carbon atoms in the alkylene are optionally replaced by —O— or —S—; and
(iii) $C_{1-24}$alkylene-OH, wherein one or more available carbon atoms in the alkylene are optionally replaced by —O— or —S—;
▬▬▬▬ represents the surface of the solid support; and
each --O-- represents an oxygen atom in the siloxane network.

In an embodiment, $R^C$ is $C_{1-24}$alkyl, —CH$_2$(CH$_2$CH$_2$O)$_i$—C(O)CF$_3$ or —CH$_2$(CH$_2$CH$_2$O)$_i$—H, wherein i is 1, 2, 3 or 4. In another embodiment, $R^C$ is $C_{14-20}$alkyl, —CH$_2$(CH$_2$CH$_2$O)$_i$—C(O)CF$_3$ or —CH$_2$(CH$_2$CH$_2$O)$_i$—H, wherein i is 2 or 3. In a further embodiment, $R^C$ is $C_{4-20}$alkyl, —CH$_2$(CH$_2$CH$_2$O)$_i$—C(O)CF$_3$ or —CH$_2$(CH$_2$CH$_2$O)$_i$—H, wherein i is 2 or 3. It is an embodiment that $R^C$ is octadecyl, 3-(2-(2,2,2-trifluoroacetoxy)ethoxy)propyl or 3-(2-hydroxyethoxy)propyl. In another embodiment of the present disclosure, $R^C$ is hexyl, octadecyl, 3-(2-(2,2,2-trifluoroacetoxy)ethoxy)propyl or 3-(2-hydroxyethoxy)propyl. In a further embodiment, $R^C$ is hexyl. In another embodiment of the present disclosure, $R^C$ is octadecyl. In a further embodiment, $R^C$ is 3-(2-(2,2,2-trifluoroacetoxy)ethoxy)propyl. In a yet further embodiment, $R^C$ is 3-(2-hydroxyethoxy)propyl.

The actin is modified with a dye that is suitable for detection by a spectroscopic method such as fluorescence spectroscopy and/or ultraviolet (UV)-visible spectroscopy. In an embodiment, the dye is suitable for detection by fluorescence spectroscopy. In another embodiment, the dye is suitable for detection by UV-visible spectroscopy. In a further embodiment, the dye is suitable for detection by fluorescence spectroscopy and UV-visible spectroscopy, for example, the actin is modified with rhodamine, optionally NHS-rhodamine. In another embodiment, the dye is suitable for detection by infrared spectroscopy.

The selection of such a dye can be made by a person skilled in the art. For example, it will be appreciated by a person skilled in the art that a suitable dye should not, for example, significantly affect actin's ability to bind to and leave gelsolin or change actin's 3D structure, and actin should not significantly affect the absorbance of the dye. It will be appreciated by a person skilled in the art that dyes such as NHS-rhodamine which target amine groups on the protein are useful, for example, as modification of amines typically has a lesser effect on protein function and structure than modifying other groups such as a thiol or a carboxylic acid. Further, for example, when the liquid sample is serum from a subject and the detection method comprises visible spectroscopy, it would be also appreciated by a person skilled in the art that the selection of a dye that has an absorption peak at a wavelength greater than about 500 nm is useful, for example, because serum has a strong absorbance in the lower visible wavelengths and the UV region which begins to trail off at 450 nm and is insignificant above 500 nm. Accordingly, in an embodiment, the actin is modified with a dye that has an absorption peak at a wavelength greater than about 500 nm. In another embodiment, the dye-modified actin is rhodamine-modified actin. The rhodamine can be linked to the actin through any suitable means, the selection of which can be made by a person skilled in the art. In an embodiment, the dye-modified actin is NHS-rhodamine-modified actin. In another embodiment of the present disclosure, the NHS-rhodamine-modified actin is modified with NHS-rhodamine that is a 5-carboxytetramethylrhodamine, succinimidyl ester, 6-carboxytetramethylrhodamine, succinimidyl ester or a combination thereof. In a further embodiment, NHS-rhodamine-modified actin is modified with NHS-rhodamine that is a combination of 5-carboxytetramethylrhodamine, succinimidyl ester and 6-carboxytetramethylrhodamine, succinimidyl ester. It will be appreciated that the rhodamine is linked to actin through amine bonds facilitated by the N-hydroxysuccinimide functionality of the NHS-rhodamine.

The solid support can be any suitable solid support that has a surface area to bind a sufficient amount of the dual protein system to allow for detection of the LPA in the methods for detecting LPA in a liquid sample of the present disclosure. For example, the solid support is capable of containing sufficient quantities of the dual protein system such that upon exposure to a sample containing about 1 μM LPA, a quantifiable amount of dye-modified actin is released into solution. This value will vary, for example, based on the instrument used to measure the solution, but can readily be determined by a person skilled in the art. In an embodiment, the detection limit for the dye-modified actin is about 10 nM, which corresponds to the release of about 10 pmol of rhodamine-modified actin into about 1 mL sample. In an embodiment, the solid support comprises, consists essentially of or consists of plastic, glass, metal, metal oxide or crystal or comprises, consists essentially of or consists of silica gel or magnetic nanoparticles. In another embodiment, the solid support comprises, consists essentially of or consists of plastic. The plastic can be any suitable plastic. For example, when the dye modifying the actin is suitable for detection by UV-visible spectroscopy, it will be appreciated by a person skilled in the art that the plastic should not have substantial absorbance at the wavelength at which the absorbance of the dye is detected. In a further embodiment, the plastic is polyethylene terephthalate glycol-modified (PETG), polyvinyl chloride (PVC), polyethylene terephthalate (PET), polypropylene (PP) or polycarbonate. PETG is an example of a plastic that is strong, robust to other chemicals and low-cost. Accordingly, it is an embodiment that the solid support comprises polyethylene terephthalate glycol-modified (PETG). In another embodiment, the solid support comprises, consists essentially of or consists of a silica gel. The term "silica gel" or "silica resin" may be used herein interchangeably. The silica gel can be any suitable silica gel. For example, it will be appreciated by a person skilled in the art that the dual protein system (gelsolin-actin pair) is about 146 Å across on its longest size and a silica gel having a pore size of about 150 Å has been found to work better than a silica gel having a pore size of about 60 Å in the present studies. Accordingly, in another embodiment, the silica gel has a pore size of about 150 Å or greater. The minimum pore size should be larger than the protein complex. In a further embodiment, the silica gel has a mesh size of about 60 to about 450 mesh, optionally about 200 to about 425 mesh. In an embodiment, from about 0.1 mL to about 2.0 mL or about 0.5 mL of silica gel is used.

In yet another embodiment, the solid support comprises, consists essentially of or consists of magnetic nanoparticles. The magnetic nanoparticles can be any suitable magnetic nanoparticles. For example, it will be appreciated by a person skilled in the art that the magnetic nanoparticles have surface functionalization suitable such that the gelsolin or linker and optionally the diluent can bind thereto as described hereinabove. In an embodiment, the magnetic nanoparticles are functionalized with a hydroxyl or carboxylic acid functionality (so as to bind e.g. a siloxane network-based SAM). Functionalization of the metal nanoparticle surface can be achieved by known means, for example, using a mixture of sulfuric acid and hydrogen peroxide. Alternatively, functionalized magnetic nanoparticles are available through commercial sources. In an embodiment, the magnetic nanoparticles are iron oxide (II,III) magnetic nanoparticles having an average particle size of about 5 nm to about 30 nm which are functionalized with hydroxyl and/or carboxylic acid functionalities.

The solid support can be in any suitable form. In an embodiment, the solid support is a testing strip, a microwell plate or a microcentrifuge tube. In another embodiment, the solid support is a testing strip. In a further embodiment, the solid support is a microwell plate. It is an embodiment of the present disclosure that the solid support is a microcentrifuge tube. In embodiments wherein the solid support is silica gel, or magnetic nanoparticles, the silica gel or magnetic nanoparticles are optionally housed and/or used in a column, vial, tube or any other suitable vessel that allows a liquid sample to be tested to be exposed thereto, optionally wherein the vessel allows the liquid sample to be exposed to the biosensor by passing through a layer of the silica gel or magnetic nanoparticles. In embodiments wherein the solid support is magnetic nanoparticles, the magnetic nanoparticles are optionally removable from the liquid sample via a magnet after exposure of the biosensor to the sample. In embodiments, where the solid support is silica gel, the solution may be passed through the gel prior to detection.

In an embodiment, the biosensor is for use in diagnosing a risk of ovarian cancer in a subject which can then be confirmed. For example, the biosensor can be used to determine whether or not a sample from a subject has an elevated level of LPA, which is a signal that the subject may, for example, have ovarian cancer. The diagnosis of ovarian cancer is then made, for example, using an imaging technique. The imaging technique can be any suitable imaging technique. In an embodiment, the imaging technique comprises transvaginal ultrasound (TVU). In another embodiment, the imaging technique comprises magnetic resonance imaging (MRI). The use of such techniques for diagnosing ovarian cancer is known to persons skilled in the art. It will be appreciated that TVU may be useful, for example, due to lower cost compared to MRI.

The present disclosure also includes a kit for detecting and/or quantifying lysophosphatidic acid (LPA) in a liquid sample, the kit comprising:
(a) a biosensor for detecting and/or quantifying lysophosphatidic acid (LPA) in a liquid sample of the present disclosure; and
(b) optionally instructions for use.

In an embodiment, the solid support of the biosensor is in the form of a testing strip, a well in a microwell plate or a microcentrifuge tube or the solid support consists essentially of silica gel or magnetic nanoparticles housed in a column, vial or tube, and:
(a) when the solid support is in the form of a testing strip, the kit further comprises one control testing strip per each 2 or 3 biosensors in the kit, the control testing strip made of the same solid support as the biosensors but not the dual protein system or linker;
(b) when the solid support is in the form of a well in a microwell plate, the microwell plate comprises one control well per each 2 or 3 biosensors in the microwell plate, the control well made of the same solid support as the biosensors but not the dual protein system or linker;
(c) when the solid support is in the form of a microcentrifuge tube, the kit further comprises one control tube per each 2 or 3 biosensors in the kit, the control tube made of the same solid support as the biosensors but not the dual protein system or linker; and
(d) when the solid support consists essentially of silica gel or magnetic nanoparticles housed in a column, vial or tube, the kit further comprises one control column, vial or tube per each 2 or 3 biosensors in the kit, the control column, vial or tube containing the same solid support as the biosensors but not the dual protein system or linker.

In an embodiment, the control testing strip, well or tube does not comprise diluent. In an alternative embodiment of the present disclosure, the control testing strip, well or tube comprises diluent. In an embodiment, the control silica gel or magnetic nanoparticles do not comprise diluent. In an alternative embodiment of the present disclosure, the control silica gel or magnetic nanoparticles do comprise diluent.

In an embodiment, the kit comprises one control testing strip, well or microcentrifuge tube, or one column, vial or tube housing silica gel or magnetic nanoparticles per each 2 biosensors. For example, such kits can be used in a method that quantifies the amount of LPA in a liquid sample, and comprises:

exposing a first portion of the sample to a first biosensor;
analyzing the first portion of the sample after exposure to the first biosensor to obtain a first signal value;
adding a known amount of LPA to a second portion of the sample;
exposing the second portion of the sample to a second biosensor;
analyzing the second portion of the sample after exposure to the second biosensor to obtain a second signal value;
exposing a third portion of the sample to a control made of the same solid support as the biosensors but not the dual protein system or linker;
analyzing the third portion of the sample after exposure to the control to obtain a control signal value; and
calculating the ratio of the first signal value minus the control signal value to the second signal value minus the control signal value to determine the concentration of LPA that was present in the sample,
wherein the first biosensor and the second biosensor are each made of the same solid support, dual protein system and linker; and
wherein the steps of analyzing comprise spectroscopically measuring a signal associated with the dye of the dye-modified actin.

In an embodiment, the kit further comprises a predetermined amount of LPA. For example, one or more of the microcentrifuge tubes, wells, columns, vials or tubes of the kit, as the case may be, contains a predetermined amount of LPA. While not wishing to be limited by theory, in the solid form, the LPA would not be predicted to bind to the gelsolin and thereby release the dye-modified actin. However, even if it does react, while not wishing to be limited by theory, the amount of actin released will be in relation to the amount of LPA added, and will, upon use of such a kit to detect and/or quantify the amount of LPA in a liquid sample, end up in the liquid of the sample.

In another embodiment, the kit is for use in diagnosing a risk of ovarian cancer in a subject which can then be confirmed. For example, the kit can be used to determine whether or not a sample from a subject has an elevated level of LPA, which is a signal that the subject may, for example, have ovarian cancer. The diagnosis of ovarian cancer is then made, for example, using an imaging technique. The imaging technique can be any suitable imaging technique. In an embodiment, the imaging technique comprises transvaginal ultrasound (TVU). In another embodiment of the present disclosure, the imaging technique comprises magnetic resonance imaging (MRI).

It will be appreciated by a person skilled in the art that the embodiments of the kits for detecting and/or quantifying lysophosphatidic acid in a liquid sample (LPA) of the present disclosure can also be varied as discussed herein for the embodiments of the biosensor for detecting and/or quantifying lysophosphatidic acid (LPA) in a liquid sample of the present disclosure.

III. Methods for Detection

In the studies of the present disclosure, a plastic strip which was made of PETG, and silica gel were treated under conditions to deposit thereon a mixed self-assembled monolayer (SAM) comprising protein probes for receiving LPA (his-tagged gelsolin) and releasing a dyed probe (actin functionalized by NHS-rhodamine dye) that can be sensed by UV-visual absorbance spectroscopy or fluorescence spectroscopy thereby creating a biosensor. The mixed self-assembled monolayer comprised a linker molecule which terminated in a nickel-NTA group which bound to the his-tag of the gelsolin. The linker molecule used in the present studies comprised an ethylene glycol moiety which may, for example, have antifouling properties in that it may, for example, prevent adsorption of interfering biomolecules to the biosensor. In the present studies, a linker/diluent system was used in the SAM in which the diluent was prepared from octadecyltrichlorosilane (OTS) or hexyltrichlorosilane (HTS) and the linker was prepared using 3-(3-(trichlorosilyl) propoxy)propanoyl chloride (Meg-Cl), to which was bound Na,Na-bis(carboxymethyl)-L-lysine hydrate (ab-NTA), creating an NTA surface which, subsequent to treatment with $NiCl_2$ to form a nickel-NTA group, bound the his-tagged protein gelsolin. In the studies of the present disclosure, the protein actin was from rabbit muscle and was modified with NHS-rhodamine causing it to absorb light at 552 nm. This protein was then added subsequent to treatment with gelsolin and bound strongly to the surface-bound gelsolin. Serum samples were introduced to the plastic testing strip or the silica gel. A time of 10 seconds was found to be a useful exposure time. Following exposure of the sample to the biosensor, the solution was removed from the biosensor and was subjected to absorbance analysis at 552 nm or fluorescence analysis of an emission wavelength of 572 nm using an excitation wavelength of 552 nm. Calibration with known samples of LPA allow for the quantification of LPA in the sample, and consequent determination of the possible presence of an ovarian tumor.

Accordingly, the present disclosure includes a method for detecting lysophosphatidic acid (LPA) in a liquid sample, the method comprising:
exposing the sample to a biosensor of the present disclosure under conditions to bind the LPA to the gelsolin and thereby release the dye-modified actin into the liquid; and
analyzing the sample after exposure to the biosensor to determine if LPA was present in the liquid sample,
wherein the step of analyzing comprises spectroscopically measuring a signal associated with the dye of the dye-modified actin.

It will be appreciated by a person skilled in the art that embodiments of the biosensor in the methods for detecting LPA in a liquid sample of the present disclosure can be varied as detailed herein for the embodiments of the biosensors for detecting and/or quantifying LPA in a liquid sample of the present disclosure.

In an embodiment, the method quantifies the amount of LPA in a liquid sample, and comprises:
exposing a first portion of the sample to a first biosensor;
analyzing the first portion of the sample after exposure to the first biosensor to obtain a first signal value;
adding a known amount of LPA to a second portion of the sample;
exposing the second portion of the sample to a second biosensor; analyzing the second portion of the sample after exposure to the second biosensor to obtain a second signal value;
exposing a third portion of the sample to a control made of the same solid support as the biosensors but not the dual protein system or linker;
analyzing the third portion of the sample after exposure to the control to obtain a control signal value; and
calculating the ratio of the first signal value minus the control signal value to the second signal value minus the control signal value to determine the concentration of LPA that was present in the sample,
wherein the first biosensor and the second biosensor are each made of the same solid support, dual protein system and linker; and wherein the steps of analyzing comprise spectroscopically measuring a signal associated with the dye of the dye-modified actin.

The solid support of each biosensor and the control can be in any suitable form. In an embodiment, the solid support of each biosensor and the control is in the form of a testing strip. In an alternative embodiment, the solid support of each biosensor and the control is in the form of a well in a microwell plate, optionally wherein the solid support of each biosensor and control are all in the same microwell plate. In a further alternative embodiment, the solid support of each biosensor and the control is in the form of a microcentrifuge tube. In an embodiment, the solid support of each biosensor and the control is in the form of a testing strip, a well in a microwell plate, silica gel or magnetic nanoparticles. In another embodiment, the solid support of each biosensor and control is in the form of silica gel housed in a column, vial or tube. In a further embodiment, the silica gel is housed in a column.

In another embodiment, the method quantifies the amount of LPA in a liquid sample, and comprises:
- exposing a first portion of the sample to a first biosensor;
- analyzing the first portion of the sample after exposure to the first biosensor to obtain a first signal value;
- adding different known amounts of LPA to each of a plurality of additional portions of the sample;
- exposing each of the plurality of additional portions of the sample to a respective plurality of additional biosensors;
- analyzing each of the plurality of additional portions of the sample after exposure to the respective plurality of additional biosensors to obtain a plurality of additional signal values;
- plotting the signal value obtained for each portion of the sample against the corresponding concentration of LPA added to the portion of the sample; and
- obtaining the concentration of LPA that was present in the sample from the y-intercept of the line of best fit for the plot, wherein the steps of analyzing comprise spectroscopically measuring a signal associated with the dye of the dye-modified actin.

It will be appreciated by a person skilled in the art that plotting the absorbance versus LPA concentration added (for UV-visible spectroscopy) or the emission versus LPA concentration (for fluorescence spectroscopy) added should give a zero point greater than the control absorbance, which corresponds to the LPA concentration that was present in the sample.

In an embodiment, the plurality of additional portions of the sample comprises three additional portions of the sample. In another embodiment, LPA is added to the first additional portion of the sample in an amount to give a concentration therein of initial +1 µM; LPA is added to the second additional portion of the sample in an amount to give a concentration therein of initial +10 µM; and LPA is added to the third additional portion of the sample in an amount to give a concentration therein of initial +25 µM.

The solid support of each biosensor can be any suitable form. In an embodiment, the solid support of each biosensor is in the form of a testing strip. In an alternative embodiment, the solid support of each biosensor is in the form of a well in a microwell plate, optionally wherein the solid support of each biosensor are all in the same microwell plate. In a further alternative embodiment, the solid support of each biosensor is in the form of a microcentrifuge tube. In an embodiment, the solid support of each biosensor is in the form of a testing strip, a well in a microwell plate, silica gel or magnetic nanoparticles. In another embodiment of the present disclosure, the solid support of each biosensor is in the form of silica gel housed in a column, vial or tube. In a further embodiment, the silica gel is housed in a column.

Spectroscopically measuring a signal associated with the dye of the dye-modified actin can be carried out by any suitable means, the selection of which can be made by a person skilled in the art. In an embodiment, the step of analyzing is carried out in situ; i.e. the sample is analyzed after exposure to the biosensor without removing the exposed sample or a portion thereof to a separate vessel for analysis. Means for analyzing a sample in situ are known and the selection of a suitable means can be made by a person skilled in the art. For example, the method can comprise using a UV-visible nano-probe or a fluorescence nano-probe, as applicable. Such nano-probes typically comprise a thin bar with fibers to carry an excitation light and another fiber to measure absorbance or emittance, as appropriate. The nano-probe can be inserted into a vessel (e.g. a microcentrifuge tube) containing the sample and the UV-visible or fluorescence signal, as applicable, measured for a period of time. In another embodiment of the present disclosure, the in situ method comprises using a biosensor wherein the solid support comprises the cuvette for a spectrometer.

In an alternative embodiment, the method further comprises, after exposing the sample to the biosensor, removing the exposed sample or a portion thereof and adding it to a separate vessel for analysis. For example, the separate vessel can be a cuvette for a UV-visible spectrometer or a fluorescence spectrometer.

In an embodiment of the present disclosure, the analyzing comprises the use of a robotic system. The robotic system can be any suitable robotic system. Robotic systems suitable for use with the methods for detecting and/or quantifying LPA in a liquid sample of the present disclosure are known. For example, certain diagnostic clinics use an automated robotic system wherein liquid samples from a patient are placed in sealed tubes with barcode identifiers. The barcode provides the robotic system with which processing techniques and tests are required for that patient's sample. This may, for example, include spinning down of blood into serum which is then used for testing, transferring of the liquid into testing strips or chambers, and measuring of the properties of, for example, the serum using one or more probes which may, for example, include absorbance spectroscopy. For example, the methods for detecting and/or quantifying LPA in a liquid sample could be carried out as a part of the robotic system. For example, the system portions serum into tubes, uses a spectrometer to measure the absorbance, and calculates the LPA concentration. The selection of a suitable system can be made by a person skilled in the art.

The sample or the portion thereof, as applicable, is exposed to the biosensor for any suitable time. The studies of the present disclosure suggest a time of at least about 10 seconds, optionally up to about 5 minutes or more may be useful to see a signal from low concentrations (i.e. <10 µM) of LPA. A time of about 25 minutes may be useful to give a complete signal plateau for any concentration. Low concentrations (i.e. <10 µM) have been observed to show slow but continued signal increase for the first 25 minutes, while larger concentrations have been observed to plateau in signal after only a few minutes. Accordingly, in an embodiment, each sample or the portion thereof, as applicable, is exposed to the biosensor for a time of about 10 seconds, about 30 seconds, about 1 minute, about 90 seconds, about 2 minutes, or about 5 minutes to about 25 minutes. In another embodiment, each sample or the portion thereof, as applicable, is exposed to the biosensor for a time of about 10 seconds to about 10 minutes. In a further embodiment, each sample or the portion thereof, as applicable, is exposed to the biosensor for a time of about 10 seconds.

The sample or the portion thereof, as applicable, is exposed to the biosensor at any suitable temperature. It will be appreciated by a person skilled in the art that heat may cause denaturation of proteins. Accordingly, in an embodiment, the temperature is from about 4° C. to about 37° C. Typically, the exposing is carried out at room temperature. Accordingly, in another embodiment, the temperature is from about 20° C. to about 25° C. Alternatively, the exposing may be carried out at refrigeration temperature. Accordingly, in another embodiment, the exposing is carried out at a temperature of about 4° C.

In an embodiment, the actin is modified with a dye suitable for detection by UV-visible absorbance spectroscopy and the step(s) of analyzing comprise(s) measuring, by ultraviolet-visible absorbance spectroscopy, a signal associated with said dye. In another embodiment, the actin is modified with a dye that has an absorption peak at a wavelength greater than about 500 nm. The selection of a suitable wavelength for measurement of the absorbance signal for a particular dye such as a particular rhodamine can be made by a person skilled in the art. For example, in an embodiment, the dye-modified actin is rhodamine-modified actin and the method comprises measuring the signal (i.e. the absorbance) at a wavelength of about 500 nm to about 590 nm. In another embodiment, the dye-modified actin is NHS-rhodamine-modified actin and the method comprises measuring the signal (i.e. the absorbance) at a wavelength of about 540 nm to about 560 nm, optionally measuring the signal at a wavelength of about 552 nm.

In an embodiment, the actin is modified with a dye suitable for detection by fluorescence spectroscopy and the step(s) of analyzing comprise(s) measuring, by fluorescence spectroscopy, a signal associated with said dye. The selection of suitable wavelengths for excitation and measurement of the emittance signal for a particular dye such as a particular rhodamine can be made by a person skilled in the art. For example, in an embodiment, the dye-modified actin is NHS-rhodamine-modified actin and the method comprises exciting the rhodamine at a wavelength of about 540 nm to about 560 nm or about 552 nm and measuring the signal (i.e. the emittance) at a wavelength of about 560 nm to about 595 nm or about 572 nm. In another embodiment of the present disclosure, the dye-modified actin is Texas Red-modified actin and the method comprises exciting the Texas Red at a wavelength of about 580 nm to about 600 nm or about 590 nm and measuring the signal (i.e. the emittance) at a wavelength of about 605 nm to about 625 nm or about 615 nm. Texas Red dye is typically attached to proteins via a sulfonyl-chloride ($SO_2Cl$) group which conjugates to the protein by reacting with an available arene functionality.

The liquid sample can be any suitable liquid sample. For example, it will be appreciated by a person skilled in the art that hospitals typically conduct tests starting with serum or whole blood. Urine could also potentially be used in the methods for detecting and/or quantifying LPA in a liquid sample of the present disclosure. It will be appreciated by a person skilled in the art that, however, the concentrations of LPA present in urine are much lower than in serum. Accordingly, in an embodiment, the liquid sample is a serum sample from a subject. In another embodiment, the liquid sample is a urine sample from a subject. In a further embodiment, the sample is a blood sample or a plasma sample from a subject and the method further comprises treating the blood sample or the plasma sample to convert it to a serum sample. Methods for converting blood samples and plasma samples to serum samples are known and the selection of a suitable method can be made by a person skilled in the art.

In another embodiment, the subject is from an at risk population for ovarian cancer. Accordingly, in another embodiment, the subject is a woman over the age of fifty and/or the woman has a family history of ovarian cancer.

Women with ovarian cancer have been reported to express LPA in serum at a level above about 1.3 µM (see: Casey et al., 1998) or above about 1.5 µM (see: Sedlakova et al., 2011) with a maximum of about 50 µM. Using a cut-off value of 1.5 µM may, for example, reduce false positives. Accordingly, in another embodiment, the concentration of LPA in the serum sample is determined to be above about 1.5 µM and the method further comprises determining whether or not the subject has ovarian cancer by a method which comprises using an imaging technique. The imaging technique can be any suitable imaging technique. In an embodiment, the imaging technique comprises transvaginal ultrasound. In another embodiment, the imaging technique comprises MRI.

IV. Compounds

In the studies of the present disclosure, mixed self-assembled monolayers were prepared which comprised a linker that bound a protein probe to a solid support. The linker used in the present studies was prepared using 3-(3-(trichlorosilyl)propoxy)propanoyl chloride (Meg-Cl). Meg-Cl comprises hydrolysable Si—Cl moieties which can react with hydroxyl groups on the surface of the solid support and with hydrolysable moieties of other linkers and diluents. Meg-Cl also comprises an acid chloride moiety which was reacted with the amine moiety of Nα,Nα-bis(carboxymethyl)-L-lysine hydrate (ab-NTA) to form an amide linkage. After treating the NTA-functionalized surface with nickel (II) chloride, the surface was functionalized with a his-tagged version of the human protein gelsolin. The linker used in the present studies contained an ethylene glycol moiety which can, for example, provide anti-fouling properties to a biosensor comprising such a system. For example, it can prevent adsorption of interfering biomolecules. It will be appreciated by a person skilled in the art that the acid chloride can also react with compounds comprising alcohol functional groups to produce ester linkages.

Accordingly, the present disclosure also includes a compound of Formula I:

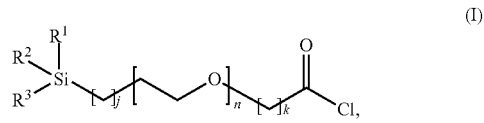

(I)

wherein $R^1$, $R^2$ and $R^3$ are each independently a hydrolysable group that does not react with an acid chloride;

j is 0, 1, 2 or 3;

k is 2, 3, 4 or 5; and n is 1, 2, 3, 4 or 5.

The hydrolysable group can be any suitable hydrolysable group so long as it does not react with an acid chloride. The selection of a suitable group can be made by a person skilled in the art. In an embodiment, $R^1$, $R^2$ and $R^3$ are each independently Cl or Br. In another embodiment, $R^1$, $R^2$ and $R^3$ are all chloro.

In an embodiment, j is 0, 1 or 2. In another embodiment of the present disclosure, j is 0 or 1. In a further embodiment, j is 0.

In an embodiment, k is 2, 3 or 4. In another embodiment of the present disclosure, k is 2 or 3. It is an embodiment that k is 2.

In an embodiment, n is 1, 2, 3 or 4. In another embodiment of the present disclosure, n is 1, 2 or 3. It is an embodiment that n is 1 or 2.

Compounds of Formula I wherein n is 1 may, for example, have a similar anti-fouling performance to corresponding compounds of Formula I wherein n is greater than 1 but may, for example, be easier and/or less expensive to synthesize. Accordingly, in another embodiment of the present disclosure, n is 1.

Compounds of Formula I wherein two carbons are between the silicon and an ether oxygen and two carbons are present between the chloracid and an ether oxygen may, for example, have useful anti-fouling performance and/or have a facile synthesis. Accordingly, in an embodiment, j is 0 and k is 2. In another embodiment of the present disclosure, j is 0, k is 2 and n is 1.

In an embodiment, the compound of Formula I has the structure:

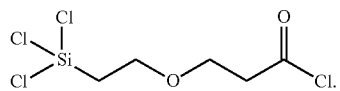

V. Methods for Preparing Biosensors

In the studies disclosed herein, mixed, self-assembling monolayers (SAMs) containing linker components and diluent components were assembled on a plastic surface, then protein probes were subsequently immobilized onto the linkers in a straightforward manner. These SAM-modified plastic test strips may be useful for detection and/or quantification of LPA in a method that is rapid and label-free. The linking molecules described herein bind to the protein probes with no detected release of the probe during testing.

Accordingly, the present disclosure also includes a method for preparing a biosensor for detecting and/or quantifying lysophosphatidic acid (LPA) in a liquid sample, the method comprising:

(a) reacting a solid support having hydroxyl groups on its surface with a compound of Formula I of the present disclosure under conditions to hydrolyze the hydrolysable groups and thereby form a self-assembled monolayer (SAM) comprising a siloxane network bound to the surface of the solid support;

(b) reacting the product obtained from (a) with an NTA moiety of the Formula II under conditions so that the acid chloride from the compound of Formula I and the amine from the compound of Formula II react to form an amide linkage:

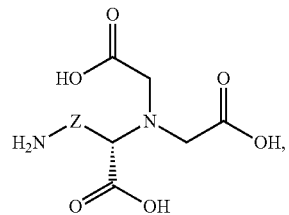

wherein
Z is $C_{2-14}$alkylene or $-(CH_2CH_2-O-)_mCH_2CH_2$; and
m is 1, 2 or 3;

(c) reacting the product obtained from (b) with a nickel (II) compound under conditions to form a complex between the $Ni^{2+}$ and the carboxylate groups from the compound of Formula II;

(d) reacting the product obtained from (c) with his-tagged gelsolin under conditions to bind the Ni-NTA moiety to the his-tag; and (e) reacting the product obtained from (d) with dye-modified actin under conditions to bind the actin to the gelsolin.

The solid support having hydroxyl groups on its surface can be any suitable solid support. In an embodiment, the solid support having hydroxyl groups on its surface comprises plastic, glass, metal, metal oxide or crystal having hydroxyl groups on its surface. In another embodiment, the solid support having hydroxyl groups on its surface comprises plastic having hydroxyl groups on its surface. In a further embodiment, the plastic is polyethylene terephthalate glycol-modified (PETG), polyvinyl chloride (PVC), polyethylene terephthalate (PET), polypropylene (PP) or polycarbonate having hydroxyl groups on its surface. It is an embodiment that the plastic is polyethylene terephthalate glycol-modified (PETG) having hydroxyl groups on its surface. Methods for modifying a surface to have a hydroxyl group thereon are known in the art and the selection of a suitable method can be made by a person skilled in the art. In an embodiment, the method comprises treating the surface with plasma under conditions to modify the surface to have a hydroxyl group thereon, for example, treating the surface with plasma for a suitable time under atmosphere. It will be appreciated by a person skilled in the art that exposing surfaces such as plastics to plasma for long periods of time will typically start to wear down the surface, for example, causing pitting. Accordingly, in an embodiment, the surface is treated with plasma for a time period of less than or equal to about 5 minutes. In yet a further embodiment, the solid support having hydroxyl groups on its surface comprises a silica gel. In an even further embodiment, the solid support having hydroxyl groups on its surface comprises functionalized magnetic nanoparticles.

It will be appreciated by a person skilled in the art that embodiments of the compound of Formula I in the methods for preparing a biosensor of the present disclosure can be varied as detailed herein for the embodiments of the compounds of Formula I of the present disclosure. In an embodiment, the compound of Formula I is 3-(3-(trichlorosilyl) propoxy)propanoyl chloride.

The conditions to hydrolyze the hydrolysable groups and thereby form a siloxane network bound to the surface of the solid support can be any suitable conditions. In an embodiment, the conditions comprise exposing the solid support to a solution comprising the compound of Formula I and reacting for a time and at a temperature for the hydrolysis of the hydrolysable groups and formation of the self-assembled monolayer (SAM) comprising a siloxane network bound to the surface of the solid support to be at least substantially complete, for example, reacting a solid support that has been exposed to a humidity chamber under conditions to provide a suitable surface hydration (for example, exposed at a relative humidity of about 80%) to the solution comprising the compound of Formula I for a time of about 15 minutes to about 4 hours or about 1.5 hours at a temperature of from about 10° C. to about 40° C. or about 25° C. Optionally, the reacting is done while agitating, for example, the reacting is carried out while on a spinning plate. It will be appreciated by a person skilled in the art that the solvent for the solution comprising the compound of Formula I should be selected such that the compound of Formula I is soluble in the solvent but is non-reactive with the solvent and the solid support is not soluble in or reactive with the solvent. For example, while anhydrous toluene is useful for silica gel and plastics such as PETG, other plastics may be soluble in anhydrous toluene therefore another hydrocarbon solvent such as anhydrous heptane may be used.

In an embodiment, Z is $C_{2-14}$alkylene. In another embodiment, Z is $C_{2-6}$alkylene. In a further embodiment, Z is —$(CH_2)_4$—.

In an embodiment, Z is —$(CH_2CH_2$—O—$)_mCH_2CH_2$. In another embodiment of the present disclosure, m is 1.

In a further embodiment of the present disclosure, the compound of Formula II is Nα,Nα-bis(carboxymethyl)-L-lysine hydrate (ab-NTA).

The conditions so that the acid chloride from the compound of Formula I and the amine from the compound of Formula II react to form an amide linkage can be any suitable conditions. In an embodiment, the conditions comprise adding an aqueous solution comprising the compound of Formula II, for example, a solution of ab-NTA in deionized water having a concentration of about 1 mg/mL to the product obtained from (a) in the presence of a suitable base, for example, triethylamine and reacting for a time and at a temperature for the reaction to be at least substantially complete, for example, a time of about 4 hours to about 24 hours or about 16 hours at a temperature from about 10° C. to about 40° C. or about 25° C. Optionally, the reacting is done while agitating, for example, the reacting is carried out while on a spinning plate.

The nickel (II) compound can be any suitable nickel (II) compound. For example, it will be appreciated by a person skilled in the art that the anions comprising the nickel (II) compound should not react with the linker. In an embodiment, the nickel (II) compound is a nickel (II) halide. In another embodiment of the present disclosure, the nickel (II) compound is $NiCl_2$.

The conditions to form a complex between the $Ni^{2+}$ and the carboxylate groups from the compound of Formula II can be any suitable conditions. In an embodiment, the conditions comprise adding an aqueous solution comprising the nickel (II) compound, for example, an aqueous solution of $NiCl_2$ having a concentration of about 1 mg/mL to the product obtained from (b) and reacting for a time and at a temperature for the complexation to be at least substantially complete, for example, a time of about 15 minutes to about 2 hours or about 1 hour at a temperature from about 10° C. to about 40° C. or about 25° C.

The conditions to bind the Ni-NTA moiety to the his-tag of the gelsolin can be any suitable conditions. In an embodiment, the conditions comprise adding an aqueous solution of gelsolin, for example, a solution of gelsolin in deionized water having a concentration of about 0.1 mg/mL to the product obtained from (c) and reacting for a time and at a temperature for the binding to be at least substantially complete, for example, a time of about 15 minutes to about 2 hours or about 1 hour at a temperature from about 10° C. to about 40° C. or about 25° C.

It will be appreciated by a person skilled in the art that embodiments of the dye-modified actin in the methods for preparing a biosensor of the present disclosure can be varied as discussed herein for the embodiments of the methods for detecting and/or quantifying lysophosphatidic acid (LPA) in a liquid sample of the present disclosure and/or the embodiments of the biosensors for detecting and/or quantifying LPA in a liquid sample of the present disclosure. In an embodiment, the dye-modified actin is NHS-rhodamine-modified actin.

The conditions to bind the actin to the gelsolin can be any suitable conditions. In an embodiment of the present disclosure, the conditions comprise adding a solution of dye-modified actin, for example, a solution of NHS-rhodamine-modified actin in Buffer A (2 mM Tris-Cl pH 8, 0.2 mM ATP, 0.5 mM 2-mercaptoethanol, 0.2 mM $CaCl_2$) to the product obtained from (d) and reacting for a time and at a temperature for the binding to be at least substantially complete, for example, a time of about 15 minutes to about 2 hours or about 1 hour at a temperature from about 10° C. to about 40° C. or about 25° C.

In another embodiment of the present disclosure, the method further comprises, in (a), reacting the solid support having hydroxyl groups on its surface with a diluent compound of Formula III under conditions to hydrolyze the hydrolysable groups and thereby form a mixed, self-assembled monolayer (SAM) comprising a siloxane network that is bound to the surface of the solid support:

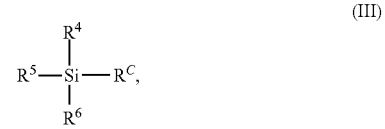

(III)

wherein
$R^4$, $R^5$ and $R^6$ are each independently a hydrolysable group that does not react with an acid chloride; and
$R^C$ is is selected from:
(i) $C_{1-24}$alkyl, wherein one or more available carbon atoms in the alkyl are optionally replaced by —O— or —S—;
(ii) $C_{1-24}$alkylene-O—C(O)CF$_3$, wherein one or more available carbon atoms in the alkylene are optionally replaced by —O— or —S—; and
(iii) $C_{1-24}$alkylene-OH, wherein one or more available carbon atoms in the alkylene are optionally replaced by —O— or —S—.

In an embodiment, $R^C$ is $C_{1-24}$alkyl, —$CH_2(CH_2CH_2O)_i$—$C(O)CF_3$ or —$CH_2(CH_2CH_2O)_i$—H, wherein i is 1, 2, 3 or 4. In another embodiment, $R^C$ is $C_{14-20}$alkyl, —$CH_2(CH_2CH_2O)_i$—$C(O)CF_3$ or —$CH_2(CH_2CH_2O)_i$—H, wherein i is 2 or 3. In another embodiment, $R^C$ is $C_{4-20}$alkyl, —$CH_2(CH_2CH_2O)_i$—$C(O)CF_3$ or —$CH_2(CH_2CH_2O)_i$—H, wherein i is 2 or 3. In a further embodiment, $R^C$ is octadecyl, 3-(2-(2,2,2-trifluoroacetoxy)ethoxy)propyl or 3-(2-hydroxyethoxy)propyl. In a further embodiment, $R^C$ is hexyl, octadecyl, 3-(2-(2,2,2-trifluoroacetoxy)ethoxy)propyl or 3-(2- hydroxyethoxy)propyl. In another embodiment, $R^C$ is hexyl. It is an embodiment that $R^C$ is octadecyl. In another embodiment, $R^C$ is 3-(2-(2,2,2-trifluoroacetoxy)ethoxy)propyl. In a further embodiment, $R^C$ is 3-(2-hydroxyethoxy)propyl.

The hydrolysable group can be any suitable hydrolysable group so long as it does not react with an acid chloride. The selection of a suitable group can be made by a person skilled in the art. In an embodiment, $R^4$, $R^5$ and $R^6$ are each independently Cl or Br. In another embodiment, $R^4$, $R^5$ and $R^6$ are all chloro.

The present disclosure also includes a biosensor prepared by a method for preparing a biosensor for detecting and/or quantifying lysophosphatidic acid (LPA) in a liquid sample of the present disclosure. It will be appreciated by a person skilled in the art that embodiments of the biosensors prepared by such methods can be varied as detailed herein for the embodiments of the methods for preparing a biosensor for detecting and/or quantifying lysophosphatidic acid (LPA) in a liquid sample of the present disclosure.

EXAMPLES

Example 1: Colorimetric Detection of Lysophosphatidic Acid (LPA)

I. Materials and Methods

The following includes detailed protocols for plastic strip cleaning, mixed self-assembling monolayer (SAM) formation, probe immobilization and ultraviolet-visible (UV-Vis) measurements. Anhydrous toluene for SAM formation and deionized water were systematically used. Octadecyltrichlorosilane (OTS) was distilled and stored in carefully sealed vials prior to use. Actin (from rabbit muscle, lyophilized powder), N-hydroxysuccinimide(NHS)-rhodamine, and Nα,Nα-bis(carboxymethyl)-L-lysine hydrate (ab-NTA) were purchased from Sigma-Aldrich®. Lysophosphatidic acid (LPA) was purchased from Enzo Life Sciences®. Plastic silanization (SAM formation) reactions were prepared in a glovebox maintained under an inert ($N_2$) and anhydrous ($P_2O_5$) atmosphere. Gelsolin plasmids were provided by Prof. Robert Robinson of the University of Singapore. UV-visible absorbance measurements were performed at 552 nm.

Plastic Strip Cleaning Procedure.

Thin pieces of polyethylene terephthalate glycol-modified (PETG) plastic (15 mm diameter circles, or 9.5×16 mm strips, and 1.5 mm thick) were first thoroughly washed 3 times with 1% sodium dodecylsulfate in deionized water (SDS), followed by sonication in SDS for 10 minutes. The strips were then thoroughly washed with 95% ethanol (EtOH) 3 times, followed by sonication for 10 minutes in EtOH. The plastic was then activated (i.e. given OH functional groups on the surface) by plasma cleaning the strips for 5 minutes under atmosphere at a pressure of about 100 mTorr. The strips were then immediately transferred into a humidity chamber, maintained at 80% relative humidity using a saturated solution of $MgNO_3 \cdot 6H_2O$, and set aside overnight.

Silanization procedure (SAM formation).

Neat linker (3-(3-(trichlorosilyl)propoxy)propanoyl chloride; Meg-Cl, 1 μL) and neat diluent (OTS, 1 μL) were diluted together with anhydrous toluene (1 mL). This solution was added to 20 mL scintillation vials each containing 3 plastic strips. The vials were capped and sealed with Parafilm™, removed from the glovebox, and placed on a spinning plate for 1.5 hours. The strips were then rinsed thrice with dry toluene and finally sonicated in toluene for 5 minutes. After a final rinse with one portion of toluene, the strips were rinsed thrice with deionized water. A solution of ab-NTA (1 mg/mL ab-NTA in deionized water, 2 mL) was added to each vial along with $Et_3N$ (30 μL), and placed on a spinning plate overnight.

Expression of Gelsolin.

pSY5 plasmids containing the Gelsolin gene with a histidine tag were introduced to bl21 Rosetta cells for expression. Cells were grown in LB buffer (37.5 g/L LB broth, 10 μg/L ampicillin, 1.5 L). Protein production was induced by isopropyl β-D-1-thiogalactopyranoside (IPTG; 1 mM) during Log phase OD 0.4-0.8 overnight. Cells were pelleted by centrifugation at 4,800 RPM for 20 minutes. Cells were re-suspended in lysis buffer (500 mM NaCl, 20 mM imidazole, 50 mM Tris pH 7.8, 0.1% Triton™ X, 5% glycerol, 1 mg/mL lysozyme, 1 protease inhibitor tablet, 4 mL), and sonicated for 30 minutes. DNAase I (1 μL) was added to the suspension, and gently rocked for 30 minutes. Cell debris was pelleted by centrifugation at 14,500 rpm for 50 minutes. Gelsolin was purified from the crude solution by use of a Ni-NTA column, followed by dialysis into storage solution (20 mM Tris pH 8.0, 0.5 mM ethylenediaminetetraacetic acid; EDTA). Protein mass and purity was determined by SDS-Page (12%), and concentration determined by absorbance at 280 nm.

Immobilization of Gelsolin.

$NiCl_2$ solution (1 mg/mL, 1 mL) was added to each strip and placed on a stirplate for 1 h. The strips were then thoroughly rinsed with deionized water. Gelsolin solution (0.1 mg/mL in deionized water, 500 μL) was added to each strip and placed on a stirplate for 1 h, followed by thorough rinsing of each strip in deionized water.

Dyeing of and Immobilization of Actin.

Actin powder was first sonicated in acetone for 5 minutes (to 1.5 mg/mL) resulting in a fine suspension. This solution was further diluted to 0.5 mg/mL with Buffer A (2 mM Tris-Cl pH 8, 0.2 mM ATP, 0.5 mM 2-mercaptoethanol, 0.2 mM $CaCl_2$)) and sonicated until all of the actin dissolved. To this solution was added NHS-Rhodamine in distilled dimethylformamide (DMF; 10 mg/mL, 1% v/v), and shaken for 90 minutes. The solution was dialized into Buffer A (GMCO 3.5 kDa). Each plastic strip containing gelsolin was exposed to 500 μL of the dyed actin solution for 60 minutes on a stirplate. The plastic strips were rinsed with deionized water and stored in Buffer A at 4° C. until used for analysis.

UV-Vis Measurements.

Each plastic strip was removed from the storage buffer, rinsed with deionized water, and exposed to a solution for testing for 25 minutes. In the present experiments, the solution was Buffer A or serum spiked with a known concentration of LPA for calibration and strip testing. In a clinical setting, for example, this can be a sample from a patient, for example serum. The solution was then removed from the strip and stored in a microcentrifuge tube until it was analyzed by UV-Vis absorbance at 552 nm. Absorbance at 552 nm was related to LPA concentration by a calibration curve.

The following includes synthetic procedures and characterization data for linker molecules as well as contact angle goniometry and X-ray photoelectron microscopy data for SAM characterization. $H_2PtCl_6 \cdot 6H_2O$ (99.9%) was purchased from Strem Chemicals Inc.®. Other chemicals were purchased from Sigma-Aldrich® and used as received unless otherwise noted. $^1H$ spectra were recorded at room temperature on Varian Mercury 300 or 400 MHz spectrometers using CDCl$_3$ as the NMR solvent. $^1$H NMR spectra are referenced to the residual solvent peak (CDCl$_3$: 7.27 ppm ($^1$H)).

Meg-Cl Synthesis.

As shown in Scheme 1, Meg-Cl 4 was synthesized in two steps from 3-(allyloxy)propanoic acid 1 with a 35% overall yield.

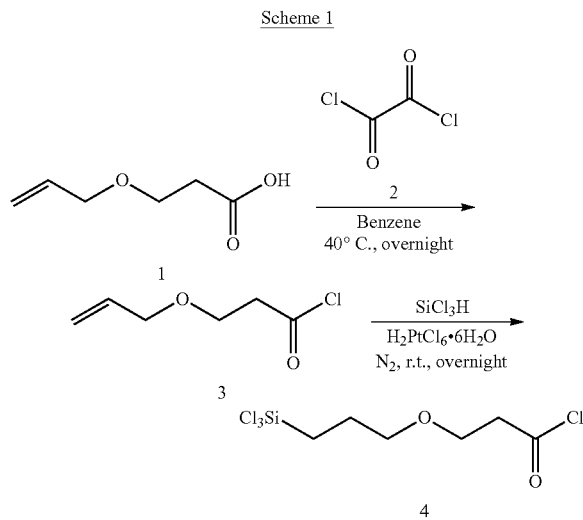

Scheme 1

3-(allyloxy)propanoic acid 1 was mixed with oxalyl dichloride 2 (8 equiv.) in benzene (200 equiv.) and stirred at 40° C. overnight. The benzene was removed under vacuum, and the resulting 3-(allyloxy)propanoyl chloride 3 was purified by Keugelrohr distillation at 140° C., resulting in a clear colourless oil (84% yield). $^1$H NMR (400 MHz, CDCl$_3$) δ 5.89 (m, 1H, J=7 Hz), 5.25 (m, 2H, J=16, 1 Hz), 4.01 (dt, 2H, J=6, 1 Hz), 3.75 (t, 2H, J=6 Hz), 3.14 (t, 2H, J=6 Hz).

To the product obtained, was added trichlorosilane (2 equiv.) and chloroplatinic acid hexahydrate (1 mol %) under a nitrogen atmosphere. The reaction was stirred at room temperature overnight. The reaction was then Keugelrohr distilled under nitrogen at 158° C. resulting in a clear colorless oil 4 (41% yield). $^1$H NMR (400 MHz, CDCl$_3$) δ 3.75 (t, 1H, J=6 Hz), 3.52 (t, 2H, J=6 Hz), 3.13 (t, 2H, 6 Hz), 1.86 (m, 2H, J=4 Hz), 1.49 (m, 2H, J=4 Hz).

Surface Analyses: Contact Angle Measurement (CAM).

Contact angle measurements (static) were performed in the Department of Chemistry, University of Toronto, Toronto, ON, Canada. Surfaces were analyzed with the KSV contact angle measurement instrument (KSV Instruments Ltd., Linthicum Heights, Md., USA) and ultrapure water as the test liquid. Contact angle values were generated using the CAM101 software.

Surface Analyses: X-Ray Photoelectron Spectroscopy (XPS).

Angle-resolved XPS analysis was performed with a Theta probe ThermoFisher Scientific Instrument (East Grinstead, UK) located at Surface Interface Ontario, University of Toronto, Toronto, ON, Canada. The samples were analyzed with monochromated Al Kα X-rays (elliptical spots of 400 ipm along the long axis), with take-off angles of 90° relative to the surface. The binding energy scale was calibrated to the main C1s signal at 285 eV. Peak fitting and data analysis were performed using Avantage software provided with the instrument (Table 1).

Angle-resolved XPS data (along with CAMs in Table 1) were used to determine whether the linker and diluent molecules had deposited from solution onto the quartz slides. Atomic percentages for characteristic elements of the linker/diluent molecules (nickel and nitrogen) along with those for elements (mainly) present in PETG (carbon and oxygen) were calculated and compared before (clean plastic strip) and after linker/diluent deposition. As expected, the clean plastic strip only showed C and O, as well as adventitious Si, while not wishing to be limited by theory, likely deposited from the vacuum chamber plastic strips are stored in. Addition of the surface linker showed a decrease in both C and O percentages, while showing a large increase in the presence of Si, as well as the appearance of Ni and N. This data along with contact angle supports the deposition of the desired surface linker on the plastic strips.

II. Results and Discussion

The present experiments studied the use of a rhodamine-modified actin and gelsolin dual protein system that is bound to a surface by a linker molecule for detecting LPA by UV-Vis spectroscopy. The linker precursor molecule used in the present studies contained a trichlorosilane moiety on one end and an acid chloride moiety on the other. However, the linker molecule itself could also be another molecule that performs the function of binding gelsolin to a surface in a covalent or non-covalent way. While the surface used in the present studies was a PETG plastic strip, other surfaces to which the protein system is bound may be used, and can include a variety of surfaces such as other plastics, glass, metals and crystals. The test may be carried out using a microwell plate, or a series of microcentrifuge tubes, for example, if a plurality of samples are being tested at once, for example, in settings such as diagnostic clinics and hospitals. Commercial sources of microcentrifuge tubes include Qiagen, Eppendorf and DiaTec.

The trichlorosilane functionality of the Meg-Cl linker reacts with hydroxyl groups present on a surface, allowing it to bind to a variety of surfaces. For example, many surfaces can be modified to contain a hydroxyl functionality including metal oxides, plastics, and metals.[15] In the present system, the acid chloride functionality on the Meg-Cl linker reacts with ab-NTA, However, this moiety can react with other entities containing amine functional groups to create amide bonds, as well as compounds containing alcohol functional groups to produce esters. As such, linkers such as Meg-Cl are useful for other uses.

Verifying the testing procedure first involved verifying the concept of the testing strip by comparing the absorbance of a solution of Buffer A that contained 25 µM LPA to the absorbance of a solution of Buffer A which did not contain LPA after having been added to a testing strip for one hour. The solution of Buffer A containing no LPA showed an average absorbance of 0.000±0.0001 (n=3), while the solution of Buffer A containing LPA showed an average absorbance of 0.051±0.002 (n=3). The lack of signal found in the lack of LPA even after one hour of exposure suggests that the gelsolin-actin complex is stably bound to the surface of the plastic, and is not non-specifically absorbed. As well, the clear signal found in the presence of LPA suggests that the test can be used in a method for detecting LPA, for example, in a cost-effective manner.

Following this, the effect of exposure time for the testing strips was studied. In order to do this, initial strips were cut from the plastic discs that were used during the first experiments. Each strip was placed in a cuvette containing Buffer A and the absorbance at 552 nm was zeroed. After verifying that there was no signal increase prior to the addition of LPA, the buffer was spiked with concentrated LPA in Buffer A (662 µM) to make the concentration in the cuvette 1, 10, or 25 µM. Each concentration was performed in triplicate. Although the error between runs of the same concentration was found to be high, which, while not wishing to be limited by theory, is likely due to the differences in surface area between testing strips used in this experiment, several results were found.

Figure 2:
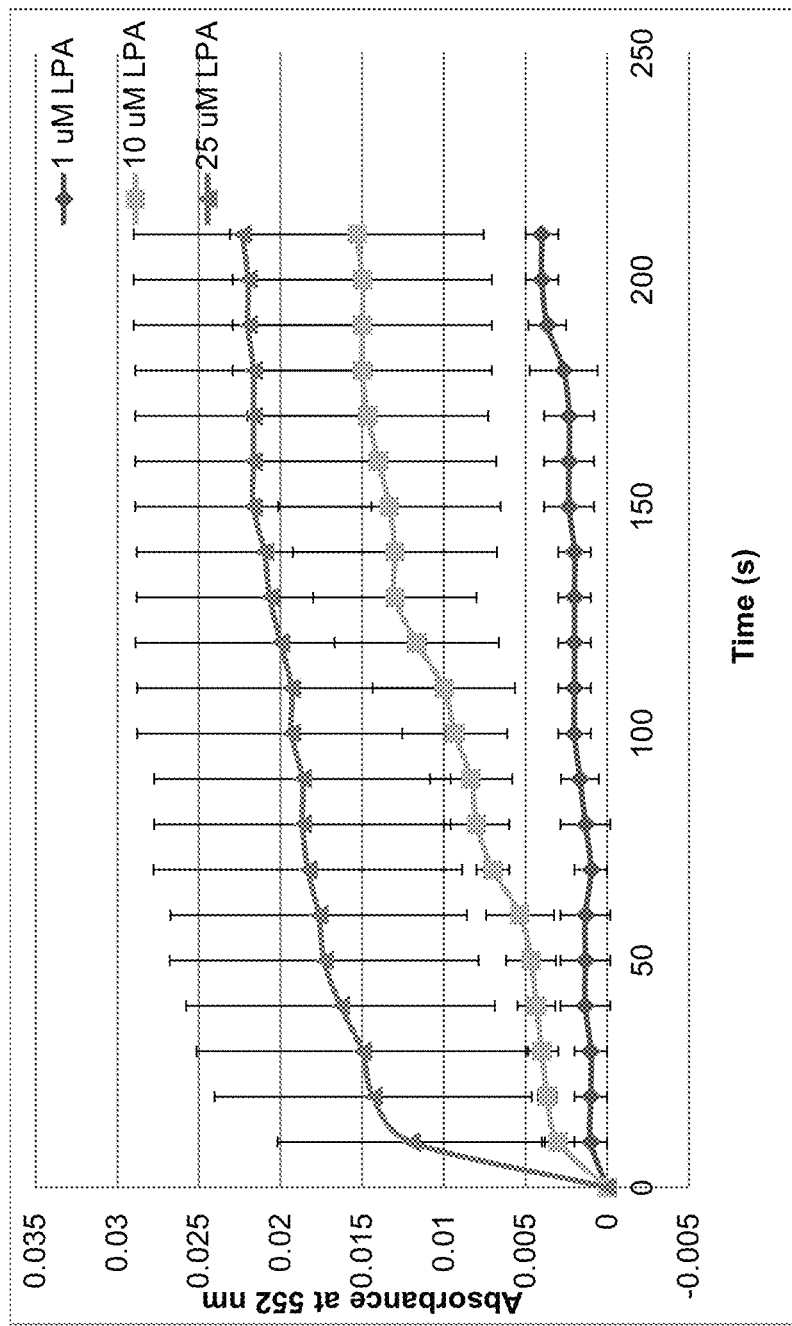
FIG. 2 is a plot showing absorbance at 552 nm measured by UV-Vis spectroscopy as a function of time (seconds) for solutions comprising various initial concentrations of LPA (1, 10, and 25 µM) exposed to biosensor testing strips according to an embodiment of the present disclosure placed in a cuvette.

First, all concentrations of LPA produced a noticeable signal within the first minute of testing. Second, higher concentrations of LPA appeared to plateau in signal faster than lower concentrations within the 3 minutes the time trials were performed for. Third, all three concentrations produced noticeably different signals at each time point for each run (FIG. 2). Although it was found that the signal for higher concentrations reached a plateau within one minute, lower concentrations, where the ability of this test to accurately determine LPA concentration is useful, were found to still be increasing after 3 minutes. It was therefore determined that future tests should be performed for at least 10 minutes in order to maximize the signal observed for low concentrations of LPA.

Figure 3:
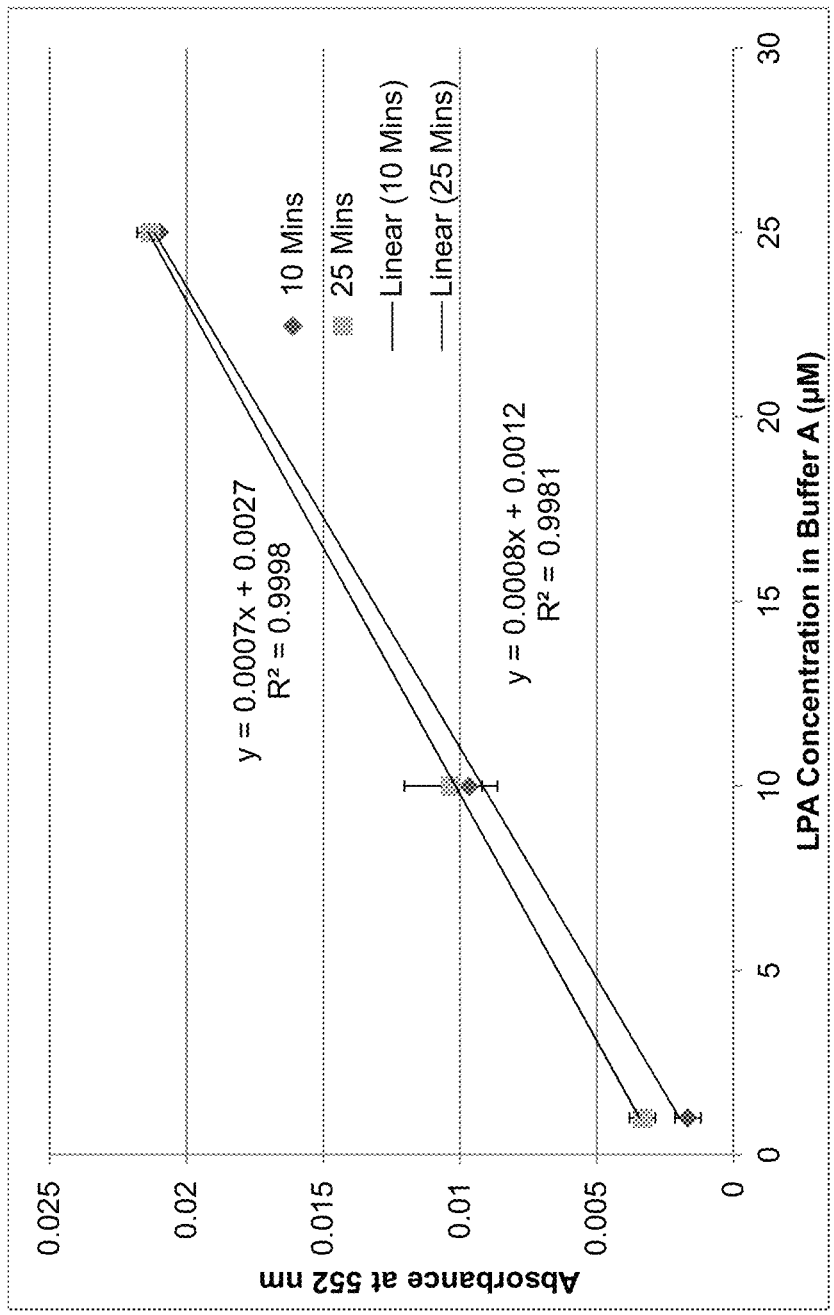
FIG. 3 is a plot showing three-point calibration curves based on absorbance at 552 nm measured by UV-Vis spectroscopy as a function of different initial LPA concentrations in Buffer A (µM) exposed to biosensor testing strips according to an embodiment of the present disclosure for 10 and 25 minutes.

An initial calibration curve in Buffer A solutions was next prepared by exposing identically sized modified testing discs to Buffer A containing known concentrations of LPA (1, 10, or 25 µM) for 10 minutes. Following measurement of the absorbance at 552 nm of the buffer solution, the discs were returned to the buffer containing LPA for a further 15 minutes. Thus, 3-point calibrations were generated at both 10 minutes and 25 minutes total exposure times (FIG. 3). These initial calibration curves were found to be linear. However, the curve at 25 minutes exposure time had a slightly higher $r^2$ value, and a higher signal at low concentrations. It was decided that 25 minutes would be a useful testing time given that it is relatively short in nature and gave a clear, linear signal.

Figure 4:
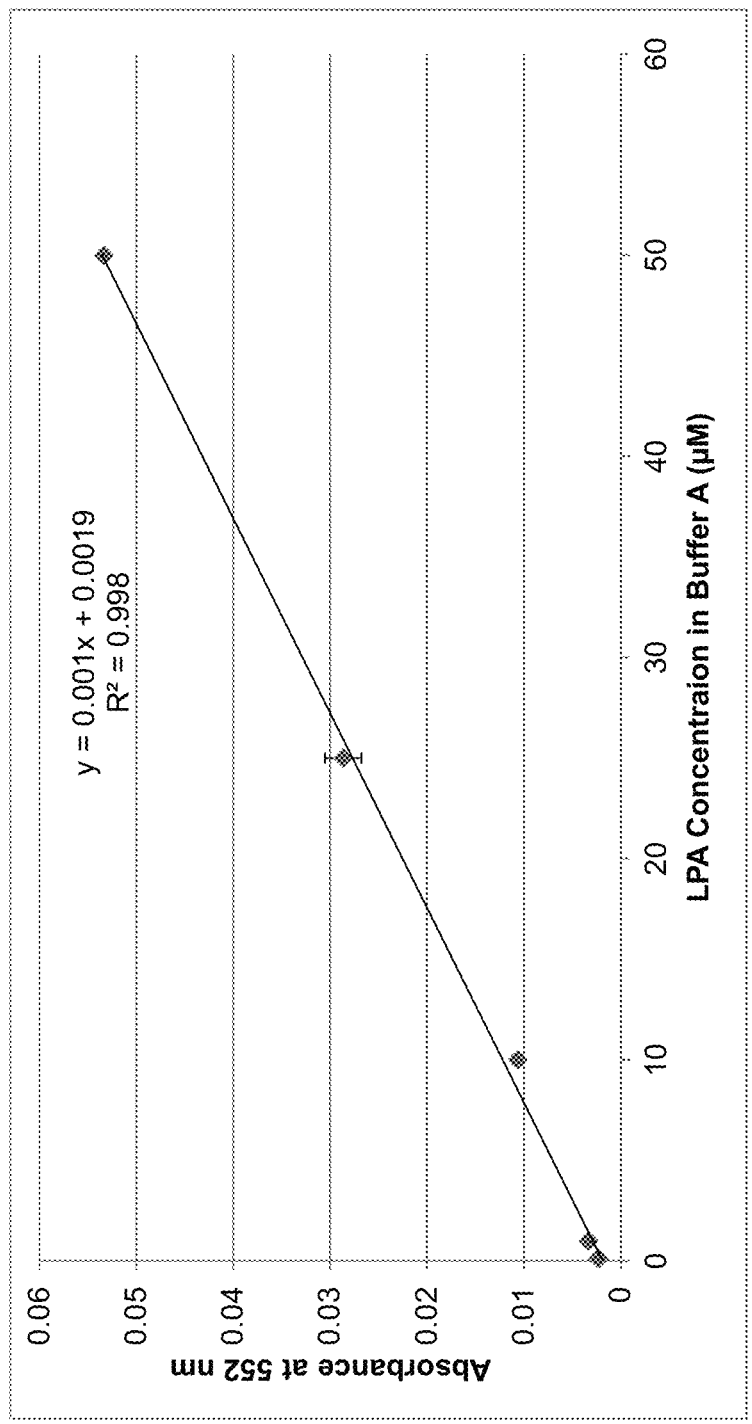
FIG. 4 is a plot showing a five-point calibration curve based on absorbance at 552 nm measured by UV-Vis spectroscopy as a function of initial LPA concentration in Buffer A (µM) exposed to biosensor testing strips according to an embodiment of the present disclosure for 25 minutes.

Following this, an extended calibration curve in buffer was made by also including 0.1 and 50 µM concentrations of LPA in Buffer A (FIG. 4). This calibration curve was also found to show good linearity along the concentration range of 0.1 to 50 µM, showing that this test has use in the quantification of LPA.

Figure 5:
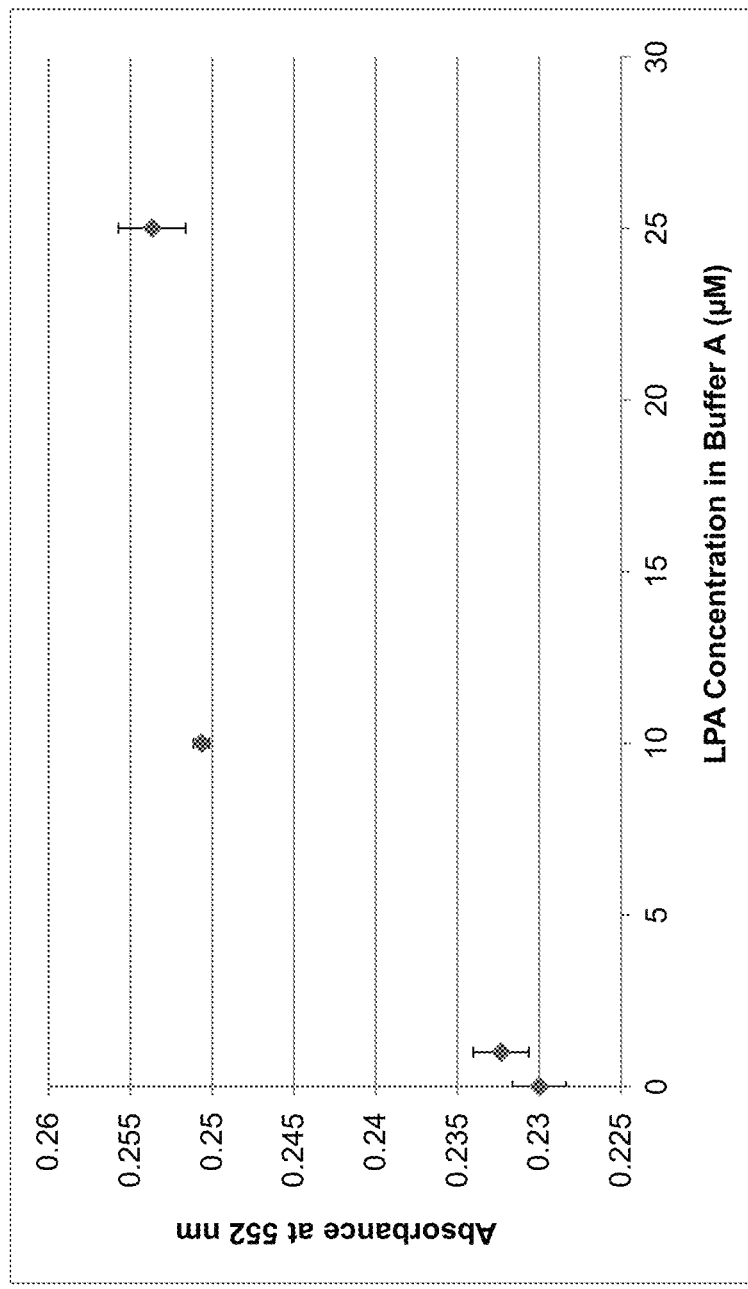
FIG. 5 is a plot showing a four-point calibration curve based on absorbance at 552 nm measured by UV-Vis spectroscopy as a function of LPA concentration in Buffer A (µM) for LPA spiked into goat serum exposed to biosensor testing strips according to an embodiment of the present disclosure for 25 minutes.

Because Buffer A provides no competing species, and no absorbance at 552 nm, it was next investigated whether the test still worked in serum samples spiked with LPA. An initial calibration curve of 25 minutes exposure to serum spiked with known concentrations of LPA (1, 10, or 25 µM) was generated with all conditions being performed in triplicate (FIG. 5). Although this calibration was found to be less linear than those generated in Buffer A, with some plateauing seen between 10 µM and 25 µM LPA concentrations, there was still a noticeable signal seen at all concentrations above that seen for discs exposed to non-spiked serum. While not wishing to be limited by theory, the lack of linearity at higher concentrations of LPA could be explained by error in LPA dilutions, signal quenching by the serum, and/or an already present and unknown concentration of LPA in the serum pushing the curve to higher unknown concentrations.

In order to determine the stability of these testing strips under storage conditions, several strips were stored in Buffer A at 4° C. and then the absorbance tested using UV-Visible spectroscopy after exposure to 25 µM LPA in Buffer A for 25 minutes. The strips were tested at 0, 7, 14, and 28 days, and all tests generated a noticeable signal (Table 2).

Each day showed fairly low error, though, while not wishing to be limited by theory, the error could be made lower, for example, by using a more rigorous preparation method of the strips, but also showed a different value than the other days. While not wishing to be limited by theory, this is most likely due to error in the concentration of LPA solution used.

In order to determine whether leaching of actin into the storage solution of Buffer A was occurring, the Buffer A used for storage at days 14 and 28 was analyzed by UV-Vis spectroscopy, and the absorbance was found to be 0.001, and 0.004 respectively (Table 2). These low signals suggest there was little leaching of actin into solution during the storage period.

Additionally, some testing strips were dried, and stored at 4° C. in air in order to study long term stability when not stored in buffer. This would, for example, allow for easier storage and handling. After 42 days of this storage the strips were exposed to either 0 µM or 25 µM LPA in Buffer A for 25 minutes. The strip exposed to 0 µM showed an absorbance of 0.0027, while those exposed to 25 µM showed an absorbance of 0.0378±0.0085 (n=3). Although the error was somewhat high in those strips exposed to LPA, while not wishing to be limited by theory, possibly due to inconsistencies in the plastic strips when they were prepared, the signal is much higher than the blank, suggesting that storage, for example, long term storage can be achieved without the need of buffer.

The test used in diagnostic settings could take multiple forms. One option is to have a test that involves one unmodified strip, well, or tube and two modified strips, wells or tubes. A sample of patient serum is added to each strip, well or tube, along with a high concentration of spiked LPA in one of the modified strips, wells or tubes. The test yields a blank signal for the unmodified strip, well or tube (the signal comprising the serum's base absorbance at 552 nm), a signal for the concentration of LPA in the patient serum, and finally a signal with maximal absorbance due to the presence of a high concentration of LPA. The ratio between the test signal minus blank over the maximal signal minus blank gives a useful measurement of LPA concentration in the sample.

Another form the test might take is a system employing four modified strips, wells or tubes where four serum samples from a patient are spiked with 0, 1, 10, and 25 µM LPA, respectively, and the absorbance tested at 552 nm. A linear trend, the slope and intercept of which would give a useful measurement of the patient's serum LPA concentration is obtained.

Example 2: Fluorescence Detection of Lysophosphatidic Acid (LPA)

I. Materials and Methods

The following includes detailed protocols for PAGE binding experiments, silica gel cleaning, mixed self-assembling monolayer (SAM) formation, probe immobilization, and fluorescence measurements. Anhydrous toluene for SAM formation and deionized water were systematically used. Octadecyltrichlorosilane (OTS) was distilled and stored in carefully sealed vials prior to use. Hexyltrichlorosilane, actin (from rabbit muscle, lyophilized powder), N-hydroxysuccinimide(NHS)-rhodamine, and Nα,Nα-bis(carboxymethyl)-L-lysine hydrate (ab-NTA) were purchased from Sigma-Aldrich®. Lysophosphatidic acid (LPA) was purchased from Enzo Life Sciences®. Silanization (SAM formation) reactions were prepared in a glovebox maintained under an inert ($N_2$) and anhydrous ($P_2O_5$) atmosphere. Gelsolin plasmids were provided by Prof. Robert Robinson of the University of Singapore. The serum used for testing was pooled male serum provided by St. Michael's hospital. Fluorescence measurements were performed with an excitation wavelength of 552 nm, and an emission wavelength of 572 nm.

Silica Gel Cleaning Procedure.

Silica gel (200-425 mesh, pore size 150 Å) was cleaned and activated (i.e. given —OH functional groups on the surface) by plasma cleaning for 5 minutes under atmosphere at a pressure of about 100 mTorr. The silica gel was then immediately transferred into a humidity chamber, maintained at 80% relative humidity using a saturated solution of $MgNO_3 \cdot 6H_2O$, and set aside overnight.

Silanization procedure (SAM formation).

Neat linker (3-(3-(trichlorosilyl)propoxy)propanoyl chloride; Meg-Cl, 3 µL) and neat diluent (hexyl trichlorosilane; HTS, 6 µL) were diluted together with anhydrous toluene (3 mL). This solution was added to 20 mL scintillation vials each containing 2 mL silica gel. The vials were capped and sealed with Parafilm™, removed from the glovebox, and placed on a spinning plate for 1.5 hours. The gel was then rinsed with dry toluene (15 mL) and finally sonicated in deionized water (5 mL) for 5 minutes. The water was removed from the gel, which was then rinsed with deionized water (15 mL). A solution of ab-NTA and $NiCl_2$ (1 mg/mL ab-NTA, 1 mg/mL $NiCl_2$ in deionized water, 4 mL) was added to the gel along with $Et_3N$ (30 4/mL), and placed on a spinning plate overnight. The gel was then washed with deionized water (20 mL).

Expression of Gelsolin.

pSY5 plasmids containing the Gelsolin gene with a histidine tag were introduced to bl21 Rosetta cells for expression. Cells were grown in LB buffer (37.5 g/L LB broth, 10 µg/L ampicillin, 1.5 L). Protein production was induced by isopropyl β-D-1-thiogalactopyranoside (IPTG; 1 mM) during Log phase OD 0.4-0.8 overnight. Cells were pelleted by centrifugation at 4,800 RPM for 20 minutes. Cells were re-suspended in lysis buffer (500 mM NaCl, 20 mM imidazole, 50 mM Tris pH 7.8, 0.1% Triton™ X, 5% glycerol, 1 mg/mL lysozyme, 1 protease inhibitor tablet, 4 mL), and sonicated for 30 minutes. DNAase I (1 µL) was added to the suspension, and gently rocked for 30 minutes. Cell debris was pelleted by centrifugation at 14,500 rpm for 50 minutes. Gelsolin was purified from the crude solution by use of a Ni-NTA column, followed by dialysis into storage solution (20 mM Tris pH 8.0, 0.5 mM ethylenediaminetetraacetic acid; EDTA). Protein mass and purity was determined by SDS-Page (12%), and concentration determined by absorbance at 280 nm.

Dyeing of Actin.

Actin powder was first sonicated in acetone for 5 minutes (to 1.5 mg/mL) resulting in a fine suspension. This solution was further diluted to 0.5 mg/mL with Buffer A (2 mM Tris-Cl pH 8, 0.2 mM ATP, 0.5 mM 2-mercaptoethanol, 0.2 mM $CaCl_2$) and sonicated until all of the actin dissolved. To this solution was added NHS-Rhodamine in distilled dimethylformamide (DMF; 10 mg/mL, 1% v/v), and shaken for 90 minutes. The solution was dialyzed into Buffer A (GMCO 3.5 kDa).

Actin/Gelsolin Binding Gels.

Solutions containing gelsolin (11 pmol) with varying amounts of rhodamine-actin (1.5-14.5 pmol) were prepared to a total volume of 10 µL in buffer (25 mM Tris pH 8, 20 µM; EDTA 0.5 µM). They were left in the fridge to bind for 1 hour. A gel was prepared (stacking gel: 25 mM Tris pH 8, 194 mM glycine, 0.2 mM ATP, 0.1% triton-X, 7.5% acrylamide, 0.2% N,N'-methylenebisacrylamide, 0.03% EDTA, 0.1% ammonium persulfate) with 10 lanes. The gel was pre-run for 30 minutes at 120 V in electrode buffer (25 mM tris pH 8, 194 mM glycine, 0.2 mM ATP, 0.5 mM $CaCl_2$). The actin/gelsolin solutions were then added to the gel and it was run for 40 minutes at 120 V. The same experiment was then performed using solutions containing 1:1 actin:gelsolin (20 pmol) with varying amounts of LPA added (1-50 µM).

Immobilization of Gelsolin and Actin.

Gelsolin and Actin solutions were mixed together in a 1:1 molar ratio, and stored in a fridge for 1 hour. For each 1 mL of silica gel 1 mL of buffer A, 1 mg of $NiCl_2$ and a protein solution containing at least 1 nmol of gelsolin and actin was added and placed on a stirplate for 1 h. The gel was then thoroughly rinsed with buffer A (15 mL per 1 mL gel).

Fluorescence Measurements.

The gel was dried under air and distributed into 1 mL plastic syringes containing a cotton plug (0.5 mL gel per syringe). In the present experiments, a solution of Buffer A or a solution of serum had its fluorescence measured, and was subsequently passed through one of the syringes containing gel, followed by a second fluorescence measurement. A solution of buffer A or serum containing imidazole (~700 µM) was then measured by fluorescence, and was subsequently passed through the same syringe as the previous solution, followed by a second fluorescence measurement. A solution of either buffer A or serum spiked with a known concentration of LPA had its fluorescence measured, and was subsequently passed through a second syringe containing gel, followed by a second fluorescence measurement. In a clinical setting, for example, this can be a sample from a patient, for example serum. All signals were determined by subtracting the first fluorescence measurement for each condition from the second fluorescence measurement. Signal due to LPA was determined by subtracting the signal from the blank solution from the signal obtained from the solution containing LPA.

II. Results and Discussion

It was found through further controls performed after the results in Example 1 were obtained that LPA itself causes a noticeable UV-Visible signal in the wavelengths tested (552 nm), and contributed to the signals obtained. Experiments with more complete controls showed some signal for LPA generated however it was not as strong or linear. It was found using imidazole (a compound used to remove proteins bound via His-tags to Ni-NTA) that the cause of this was a too small amount of protein on the surface of the PETG plastic strips; a limitation caused by lack of surface area.

Fluorescence-based experiments were then conducted in which LPA was found not to fluoresce and thus not interfere with the signal from rhodamine dyed actin. However, it was found that PETG plastic strips lacked a surface area to trap a useful amount of protein for detection of LPA using the present set-up. High surface area solid supports were then tried; including standard store bought Ni-NTA resin, as well as modified silica gel.

The store bought Ni-NTA resin was found not to work as it did not bind gelsolin-actin complex in sufficient amounts to detect biologically relevant concentrations of LPA, but silica gel (commonly used in column chromatography) modified with the linker system described herein was found to trap a large amount of gelsolin and actin, and, as described in greater detail below, allowed a signal specific to LPA in both buffer and serum to be detected.

The present experiments studied the use of a rhodamine-modified actin and gelsolin dual protein system that is bound to a surface by a linker molecule for detecting LPA by fluorescence spectroscopy. The linker precursor molecule used in the present studies contained a trichlorosilane moiety on one end and an acid chloride moiety on the other. However, the linker molecule itself could also be another molecule that performs the function of binding gelsolin to a surface in a covalent or non-covalent way. While the surface used in the present studies was silica gel, other surfaces to which the protein system is bound may be used, and can include a variety of surfaces such as other plastics, glass, metals and crystals.

Figure 6:
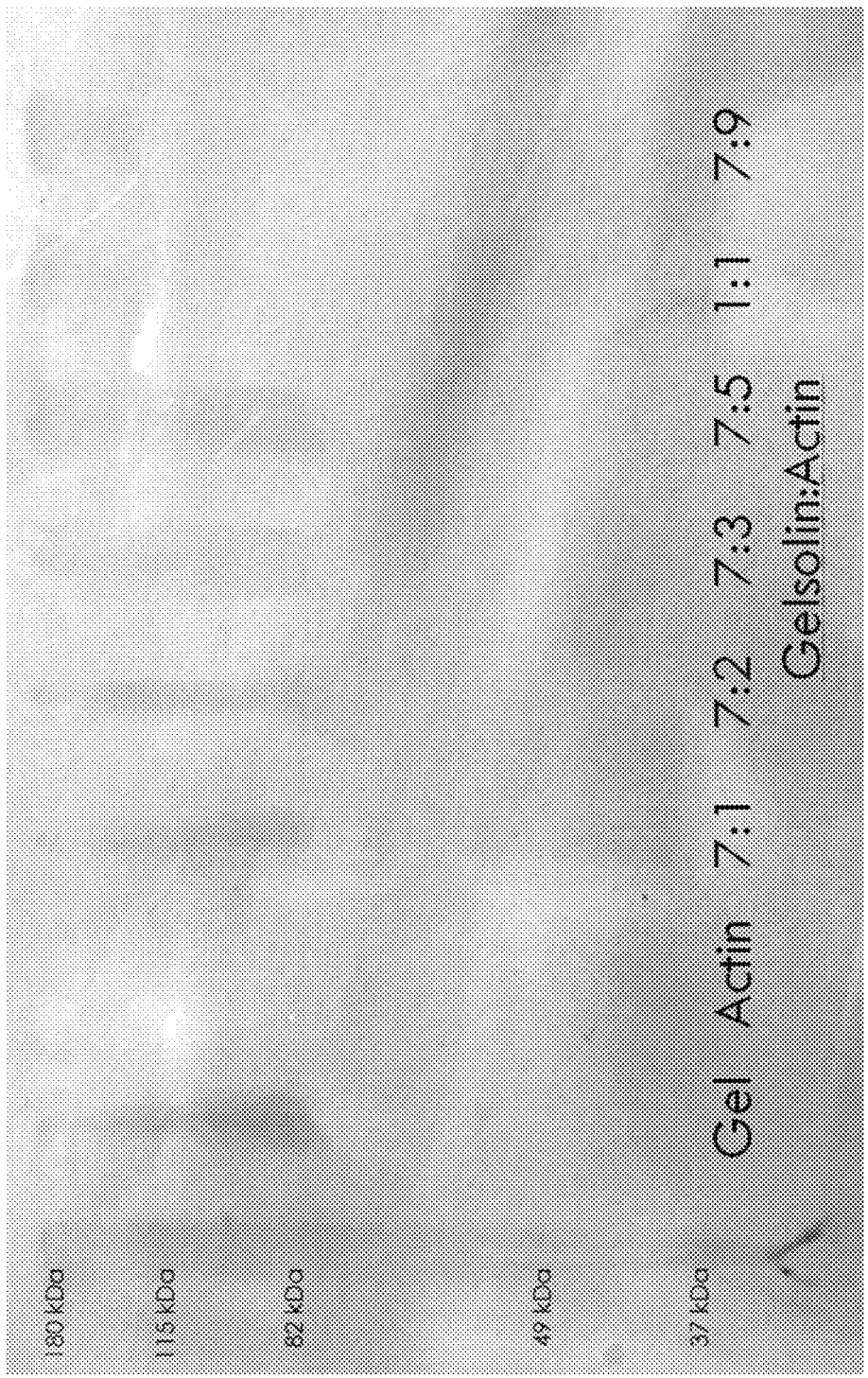
FIG. 6 shows an image of an exemplary non-denaturing PAGE gel to determine the binding ratio of gelsolin and rhodamine-actin in buffered solution. Gelsolin can be seen in each lane as a wide band at 82 kDa, while a gelsolin-actin complex can be seen as a narrower band at 180 kDa.

The binding of gelsolin and rhodamine-actin together, as well as the fluorescence of rhodamine-actin in serum in the presence of LPA was first tested to ensure the feasibility of the gelsolin-actin system in the detection of LPA. A non-denaturing PAGE experiment was performed on solutions containing various ratios of gelsolin and rhodamine-actin (FIG. 6). It was found that gelsolin can bind to rhodamine modified actin in a 1:1 ratio. The actin itself cannot be seen on the gel due to band broadening as a result of the gel being run at a high voltage. However, even with the band broadening it can still be seen that gelsolin is still able to bind actin when that actin has been modified with rhodamine dye.

Figure 7:
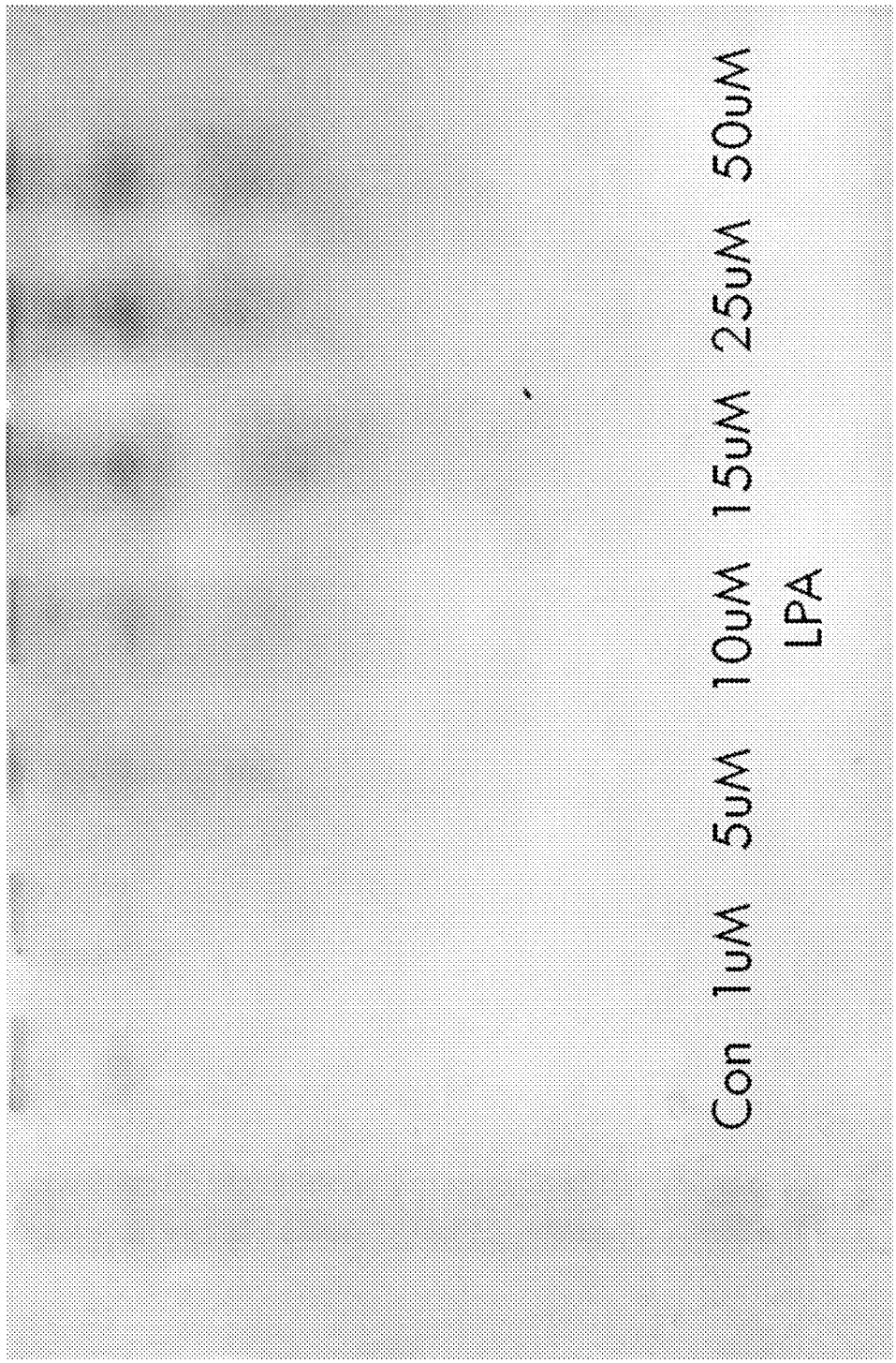
FIG. 7 shows an image of an exemplary non-denaturing PAGE gel with each lane containing a 1:1 gelsolin:rhodamine-actin solution, and a varying amount of LPA (from left to right: Con (0 µM), 1 µM, 5 µM, 10 µM, 15 µM, 15 µM and 50 µM).

A similar gel was run using a 1:1 ratio of gelsolin:rhodamine-actin in each lane, with a varying concentration of LPA in order to determine if LPA still interrupts the gelsolin/actin complex in the presence of rhodamine dye (FIG. 7). Each lane shows a band at the top, which is likely to be the gelsolin/actin protein complex. As the concentration of LPA in each lane is increased, two bands (gelsolin and actin) become visible, and darken with each increasing amount of LPA. This shows that LPA is able to disrupt the gelsolin/actin complex in the presence of rhodamine, and does so in a concentration-dependent manner. As there is still a band at the top of the gel even in the presence of the highest concentration of LPA tested, it was determined that biologically relevant concentrations of LPA do not fully disrupt this binding, which, while not wishing to be limited by theory, would suggest that large amounts of the protein complex should be used on a surface in order to see the effects of low concentrations of LPA.

Figure 8:
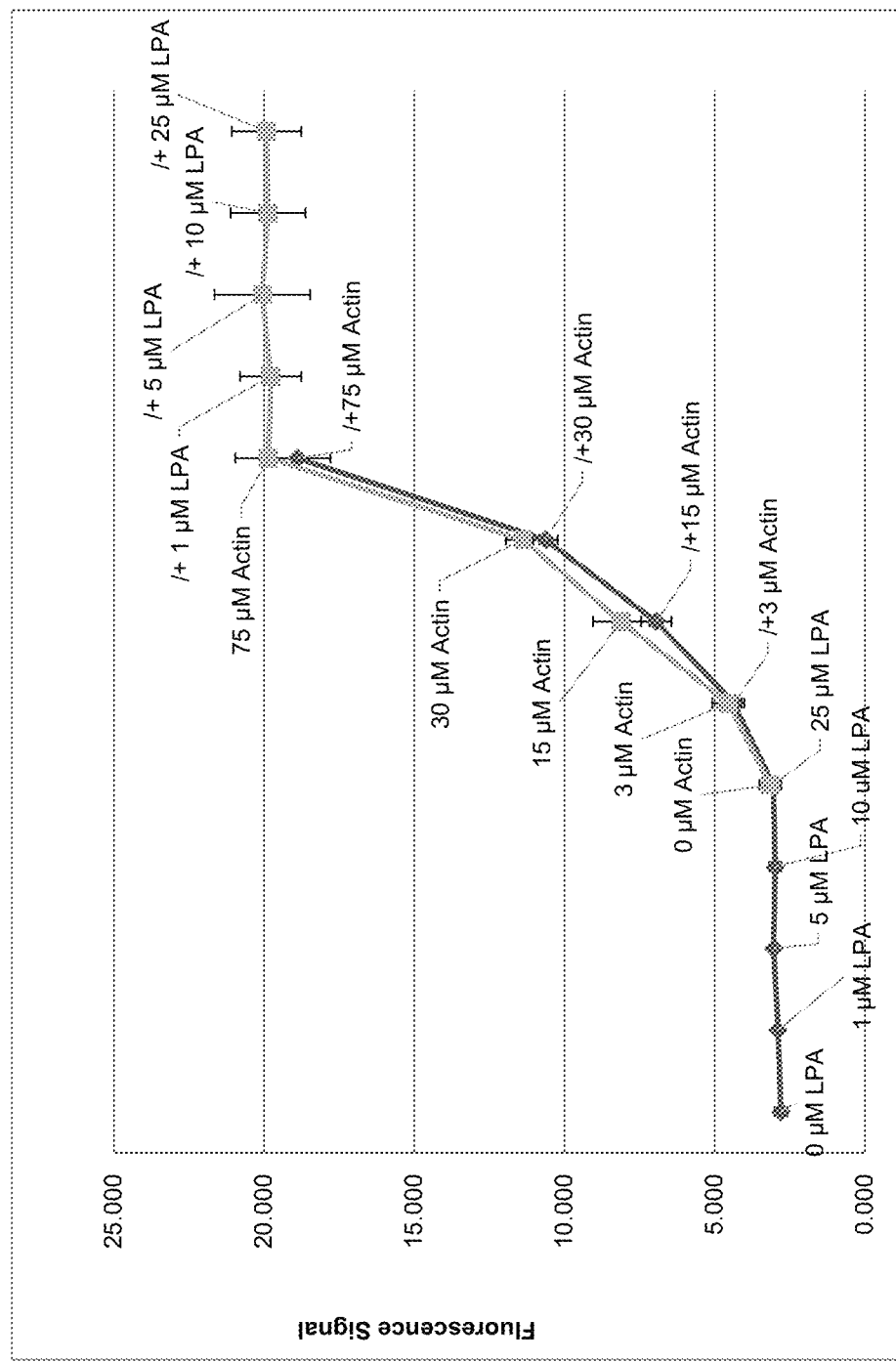
FIG. 8 is a plot showing fluorescence measurements of a serum sample to which has been added rhodamine-actin in increasing amounts (3, 15, 30 and 75 µM) followed by the addition of LPA (1, 5, 10 and 25 µM) (light grey line), and a serum sample to which has been added LPA in increasing amounts (1, 5, 10 and 25 µM) followed by the addition of rhodamine-actin (3, 15, 30 and 75 µM) (dark grey line line). The x-axis is not to scale.

In order for this test to be used, the fluorescence of rhodamine-actin in serum should, for example, be easily measured, and not be affected by the presence of LPA. A serum sample had its fluorescence measured, followed by adding increasing amounts of rhodamine-actin to it and measuring the fluorescence at each addition. This was followed by adding LPA to the serum in increasing amounts and again measuring the fluorescence at each addition. The experiment was performed again with fresh serum, but this time the LPA was added first followed by addition of rhodamine-actin (FIG. 8).

In both instances, the addition of LPA caused no change in the measured fluorescence signal, while increasing concentrations of rhodamine-actin caused an increase in fluorescence measured, which was found to be the same regardless of when the LPA is added to the solution. Although in FIG. 8, the increase in fluorescence does not appear to be linear, this is due to the x-axis not being in scale as a result of displaying both LPA and rhodamine-actin. The relationship between rhodamine-actin concentration and fluorescence is in fact linear with a limit of detection of 2.7 nM. This shows that using fluorescence it is possible to quantify rhodamine-actin in serum. Combined with the previous data on non-denaturing gels, it can be seen that a test using a gelsolin/rhodamine-actin complex bound to a solid support is useful to quantify the concentration of LPA in human serum.

In order to maximize the amount of protein complex present for the test, a high surface area solid support may be used. Silica gel, which is commonly used in column chromatography, was chosen due, for example, to its ease of use, high surface area, and low cost.

Three samples were tested for each gel condition. These were a blank solution which was either Buffer A or serum to act as a negative control, a positive control made up of imidazole dissolved the chosen medium, and finally a testing solution containing a known concentration of LPA dissolved in the chosen medium. An LPA concentration of 25 µM was chosen since it is relatively high while still being in the biologically relevant range.

Figure 9:
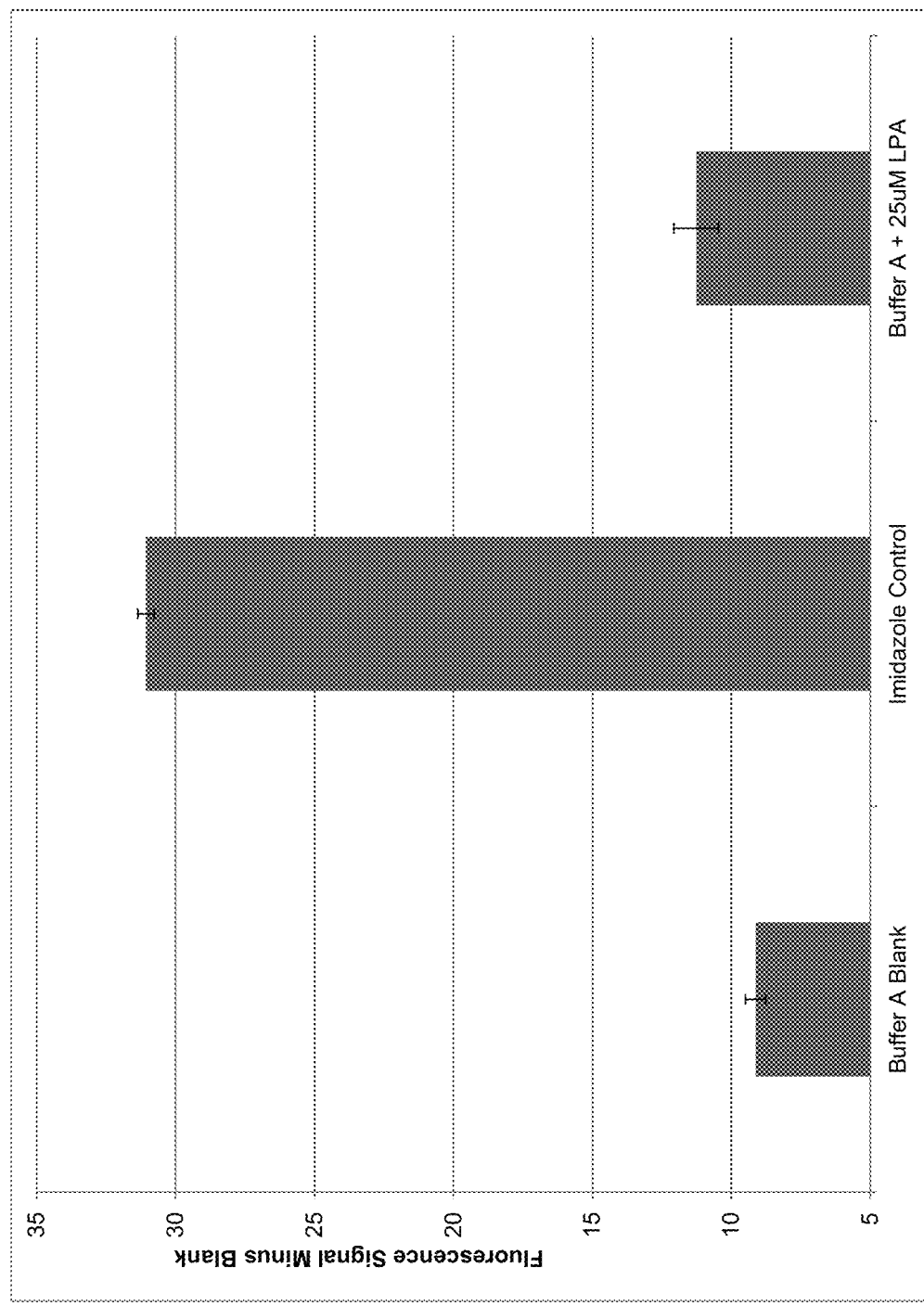
FIG. 9 shows a plot of fluorescence measurements for Buffer A samples passed over gelsolin/actin modified silica gel, from left to right: Blank, Imidazole Control and Buffer A +25 µM LPA. All values are the change in fluorescence from before being passed over the silica gel to after.

Initial tests in Buffer A found that gel with a 150 Å pore size prepared with a 1:2 Meg-Cl:HTS linker:diluent system provided the largest signal for both LPA and imidazole samples (FIG. 9). A signal for the blank Buffer A solution shows a fluorescence increase after passing over the gel. While not wishing to be limited by theory, this suggests that some rhodamine-actin is non-specifically adsorbed to the gel surface. The amount of non-specifically adsorbed proteins should be reduced in order to minimize conflicting signal with specifically bound actin that is released by LPA.

Despite the fluorescence found in the blank solution, a large fluorescence signal was found for the positive imidazole control solution. Imidazole is able to break the bond between his-tags and Ni-NTA, and thus will release any specifically bound protein from the gel. As the imidazole control was passed through the same column after the blank, the signal obtained should be from specifically bound protein only. The strength of the signal compared to the blank (FIG. 9) suggests that there is a large amount of gelsolin/actin complex bound to the gel.

Finally, after passing 25 µM LPA over the gel a larger signal is produced than the signal found for the blank Buffer A. Thus, the gel can be used to determine the presence of LPA in solution. Calibration curves can be made in order to accurately quantify the levels of LPA in the sample.

Figure 10:
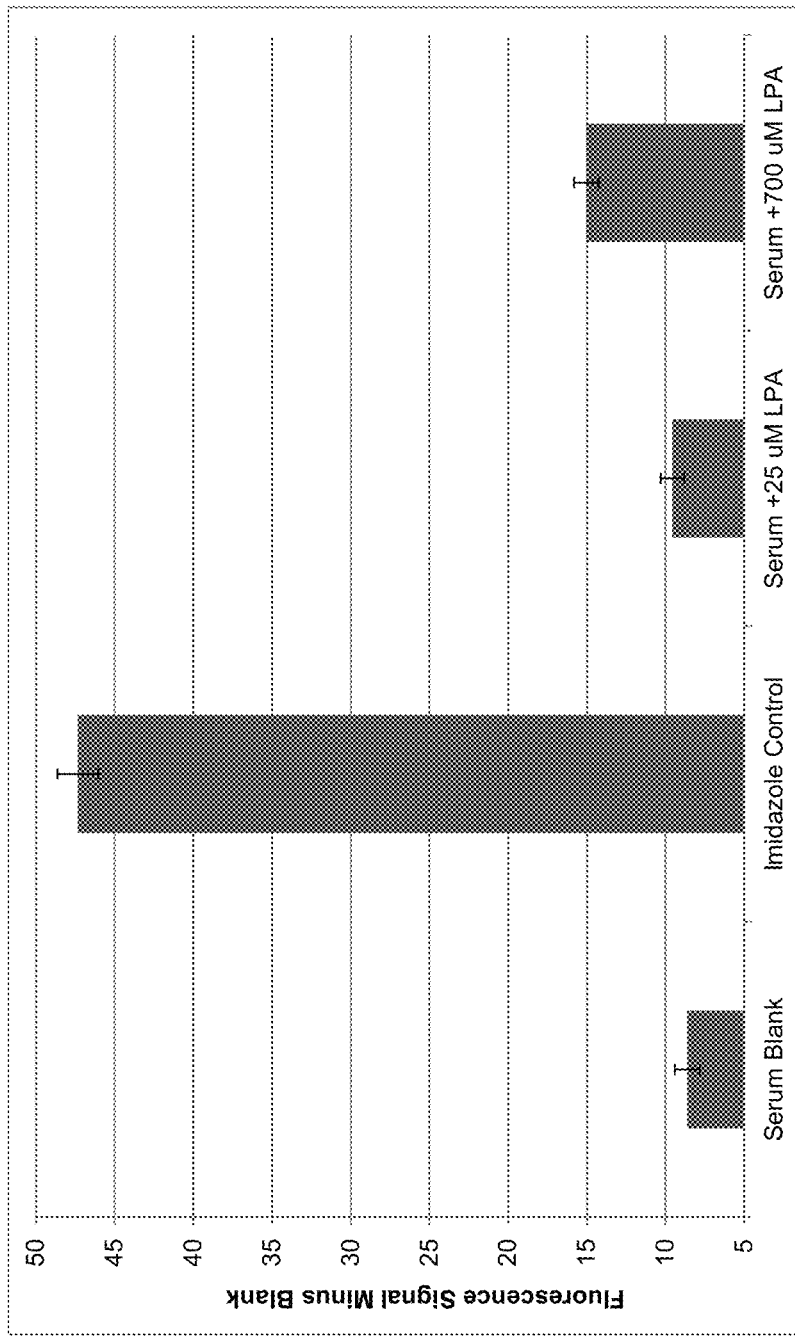
FIG. 10 shows a plot of fluorescence measurements for serum samples passed over gelsolin/actin modified silica gel; from left to right: Blank, Imidazole Control, Serum+25 µM LPA, Serum+700 µM LPA. All values are the change in fluorescence from before being passed over the silica gel to after.

In order for this test to function in a clinical setting the medium analyzed must be a biologically relevant liquid sample known to contain LPA such as serum, whole blood or urine. To this end, an experiment including an additional 700 µM LPA sample was performed using male human serum (pooled from serum sampled obtained from St. Michael's hospital). Male serum was used in order to minimize the amount of background LPA that could be present in serum samples from women. When performed in serum the results were similar to those found for the buffer A solutions, with some signal generated in the blank solution, but a much larger signal found for the imidazole control (FIG. 10). A smaller, but still detectably different signal was found for the test containing 25 µM LPA. A further solution containing 700 µM LPA was also passed through the gel, and it produced a larger signal than the 25 µM sample. The strength of the signal is dependent on the concentration of LPA.

The test used in diagnostic settings could take multiple forms. One option is to have a test that involves one column, vial or tube containing unmodified gel, and one column, vial or tube containing modified gel. A sample of patient serum is added to each column, vial or tube. The test yields a blank signal for the unmodified gel (the signal comprising the serum's base fluorescence at 572 nm), and a signal for the concentration of LPA in the patient serum. The difference between the test signal and blank gives a useful measurement of LPA concentration in the sample.

Another form the test might take is a system employing two columns, vials or tubes of modified gel and one of unmodified. In this case two of the columns, vials or tubes would be run as above, but the second modified column, vial or tube would also have an addition of LPA added to it. The ratio between the test without added LPA minus the blank, and the test with added LPA minus the blank would give a concentration of LPA.

Further Discussion

The biosensors of the present studies may be used to signal the presence of a condition which is associated with elevated levels of LPA, for example ovarian cancer or breast cancer. Diagnosis of ovarian cancer would use a further test such as transvaginal ultrasound (TVU). Breast cancer would be diagnosed by a mammogram. Ovarian cancer is difficult to detect in early stages, and TVU is expensive. Accordingly, the biosensors of the present studies may be used to provide early potential signaling for women, for example, on a yearly basis that is cheap and non-invasive. If a high concentration of LPA is found, then the subject is sent for TVU. Yearly TVUs for women without such pre-screening would be costly and overly invasive. This may therefore be useful for hospitals. Presently it is typically not possible to directly diagnose ovarian cancer without a TVU and such a test could be used to signal who should get a TVU.

The gelsolin-actin complex is primarily dissociated by LPA. While other lipids are known to cause small amounts of actin release, it is at much lower amounts than observed for LPA. For example, the main other lipid that could interfere with the test is lipopolysaccharide (LPS), which releases actin at 50% of the amount that LPA does. However, LPS is not a human lipid; it is bacterial in origin and therefore only would be present in patients suffering from sepsis. The physician treating such a patient would typically already be aware of sepsis in such a case. Lysophosphatidylcholine (LPC) is another lipid which may dissociate actin from gelsolin. However, LPC only releases actin at about 10% of the activity of LPA and is also typically found at a lower concentration relative to LPA in serum samples. Accordingly, the presence of LPC in serum samples should not significantly interfere with the test[16] Sphingosine-1-phosphate (S-1-P) is also mentioned in the Meershaert et al. article[16] and has an actin release in the order of about 10% of the activity of LPA as well. S-1-P typically exists at a concentration of 1 µM in human serum, so it also should not significantly interfere with the test.

LPA exists in multiple forms based on the linkage between the phosphate group and the fatty acid chain, as well as the chain length and saturation. The 18:2 acyl linked form of LPA is the most common in human bodily fluids, with other chain lengths and linkages present in lower concentrations[17]. People carry roughly the same ratios of the different LPA species[17]. Accordingly, while not wishing to be limited by theory, even if LPA species have different activities for dissociating actin from gelsolin, as everyone's ratio is the same, the results will only be affected by total LPA concentration.

While the present disclosure has been described with reference to what are presently considered to be the preferred examples, it is to be understood that the disclosure is not limited to the disclosed examples. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE DESCRIPTION

[1] Stevens, G. A.; Mathers, C. A.; Beard, J. R., *Bull. World Health Organ.*, 2013, 91, 630-639.

[2] Vaughan, S.; Coward, J. I.; Bast, R. C. Jr.; Berchuck, A.; Berek, J. S.; Brenton, J. D.; Coukos, G.; Crum, C. C.; Drapkin, R.; Etemadmoghadam, D.; Friedlander, M.; Gabra, H.; Kaye, S. B.; Lord, C. J.; Lengyel, E.; Levine, D. A.; McNeish, I. A.; Menon, U.; Mills, G. B.; Nephew, K. P.; Oza, A. M.; Sood, A. K.; Stronach, E. A.; Walczak, H.; Bowtell, D. D.; Balkwill, F. R., *Nat. Rev. Cancer,* 2011, 11(10), 719-725.

[3] Jemal, A.; Bray, F.; Center, M. M.; Ferlay, J.; Ward, E.; Forman, D., *CA Cancer J. Clin.,* 2011, 61, 69-90.

[4] National Cancer Institute. SEER Cancer of the Ovary (Invasive) Incidence and Death Rate 2006-2010. http://seer.cancer.gov/csr/1975_2010/browse_csr.php?sectionSE L=21&page SEL=sect_21_table.07.html (assessed Jan. 8, 2015).

[5] Coleman, M. P.; Forman, D.; Bryant, H.; Butler, J.; Rachet, B.; Maringe, C.; Nur, U.; Tracey, E.; Coory, M.; Hatcher, J.; McGahan, C. E.; Turner, D.; Marrett, L.; Gjerstorff, M. L.; Johannesen, T. B.; Adolfsson, J.; Lambe, M.; Lawrence, G.; Meechan, D.; Morris, E. J.; Middleton, R.; Steward, J.; Richards, M. A., *Lancet,* 2011, 377, 127-138.

[6] National Cancer Institute. SEER Cancer of the Ovary (Invasive) 5 Year Survival 2003-2009. http://seer.cancer.gov/csr/1975_2010/browse_csr.php?sectionSEL=21&page SEL=sect_21_table.08.html (assessed Jan. 8, 2015).

[7] Torpy, J. M. *JAMA,* 2011, 305(23), 2484.

[8] Mohagheg, P.; Rockall, A. G. *Radiographics,* 2012, 32, 1751-1773.

[9] Sharma, A.; Apostolidou, S.; Burnell, M.; Campbell, S.; Habib, M.; Gentry-Maharaj, A.; Amso, N.; Seif, M. W.; Fletcher, G.; Singh, N.; Benjamin, E.; Brunell, C.; Turner, G.; Rangar, R.; Godfrey, K.; Oram, D.; Herod, J.; Williamson, K.; Jenkins, H.; Mould, T.; Woolas, R.; Murdoch, J.; Dobbs, S.; Leeson, S.; Cruickshank, D.; Fourkala, E. O.; Ryan, A.; Parmar, M.; Jacobs, I.; Menon, U., *Ultrasound Obstet. Gynecol.,* 2012, 40, 338-344.

[10] Valentin, L.; Ameye, L.; Testa, A.; Lécuru, F.; Bernard, J.; Paladini, D.; Van Huffel, S.; Timmerman, D., *Gynecologic Oncology,* 2006, 102, 41-48.

[11] Kobayashi, E.; Ueda, Y.; Matsuzaki, S.; Yokoyama, T.; Kimura, T.; Yoshino, K.; Fujita, M.; Kimura, T.; Enomoto, T., *Cancer Epidemiol Biomarkers Prev.* 2012.

[12] Pagés, C.; Simon, M.; Valet, P.; Saulnier-Blache, J. S., *Prostoglandins & other Lipid Mediators.* 2001. 64, 1-10.

[13] Xu, Y.; Shen, Z.; Wiper, D. W.; Wu, M.; Morton, R. E.; Elson, P.; Kennedy, A. W.; Belinson, J.; Markman, M.; Casey, G., *JAMA.* 1998. 280(8), 719-723.

[14] Sedláková, I.; Vávrová, J.; Tošner, J.; Hanousek, L., *Tumor Biol.* 2011. 32, 311-316.

[15] Blaszykowski, C.; Shiekh, S.; Benvenuto, P.; Thomspon, M., *Langmuir,* 2012, 28(5), 2318-2322.

[16] Meershaert, K.; et al., *The EMBO Journal,* 1998, 17(20), 5923-5932.

[17] Shan, L.; et al. *J. Chromatogr. B,* 2008, 864(1-2), 22-28.

TABLE 1

Contact angle and 90° XPS analysis.

| Surface | Cleaned Plastic Strip | Meg-NTA/OTS SAM |
|---|---|---|
| Contact angle | 80.5 ± 6.0° | 54.2 ± 10.8° |
| % C1s 285 eV | 81.60 | 77.42 |
| % O1s 531 eV | 17.31 | 4.01 |
| % Si2p 100 eV | 0.36 | 13.95 |
| % Ni2p 858 eV | 0.00 | 0.60 |
| % N1s 400 eV | 0.00 | 0.94 |

TABLE 2

Stability trial of plastic testing strips stored in Buffer A.

| Storage Time | Absorbance at 552 nm for 25 μM LPA | Absorbance at 552 nm for storage solution |
|---|---|---|
| Day 0 | 0.0120 ± 0.0002 | N/A |
| Day 7 | 0.0227 ± 0.0059 | N/A |
| Day 14 | 0.0332 ± 0.0011 | 0.0010 |
| Day 28 | 0.0238 ± 0.0023 | 0.0040 |

The invention claimed is:

1. A method for detecting and/or quantifying lysophosphatidic acid (LPA) in a liquid sample for quantifying a risk of ovarian cancer, the method comprising:
 a. exposing the sample to a biosensor, the biosensor comprising:
  i. a solid support;
  ii. a dual protein system comprising gelsolin with a histidine tag and a dye-modified actin which is bound to an actin-binding site of the gelsolin through a reversible non-covalent binding;
   wherein the gelsolin is bound to the solid support via a linker, wherein the linker has the following structure:

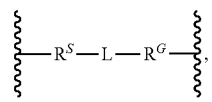

wherein $R^S$ is a functional group covalently bonded to the solid support;

L is $C_{2-20}$alkylene, or $C_{2-20}$alkylene wherein one or more available carbon atoms in the alkylene are replaced by —O— or —S—;

$R^G$ comprises a Ni-NTA moiety that is bonded to the histidine tag of the gelsolin, the Ni-NTA moiety having the following structure that is coordinated to a $Ni^{2+}$ ion:

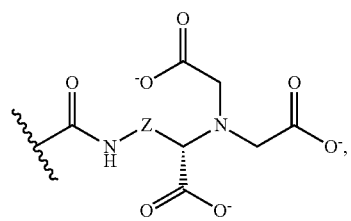

wherein

Z is $C_{2-14}$alkylene or —$(CH_2CH_2$—O—$)_m CH_2CH_2$—; and m is 1, 2 or 3;

wherein the exposure of the sample to the biosensor binds the LPA to the gelsolin and thereby releases the dye-modified actin into the liquid;

analyzing the sample after exposure to the biosensor to determine if LPA is present in the liquid sample, wherein the step of analyzing comprises spectroscopically measuring a signal associated with the dye of dye-modified actin, wherein the presence of LPA in the sample diagnoses a risk of ovarian cancer.

2. The method of claim 1, wherein L is —$(CH_2)_2$—O—$(CH_2)_2$—.

3. The method of claim 1, wherein $R^S$ comprises a silicon atom and the linker is bound to the solid support via a silicon-oxygen bond.

4. The method of claim 1, wherein the linker is comprised in a self-assembled monolayer (SAM) that is on a surface of the solid support and the SAM comprises a siloxane network comprising linkers of the following structure:

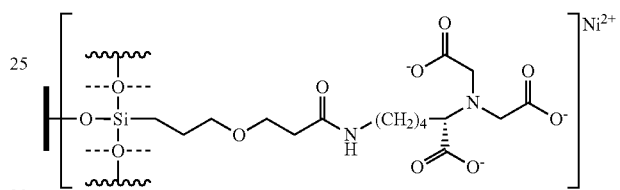

wherein

▬ represents the surface of the solid support; and each ⋅⋅⊖⋅⋅ represents an oxygen atom in the siloxane network.

5. The method of claim 1, wherein the SAM is a mixed SAM and the siloxane network further comprises diluents of the following structure

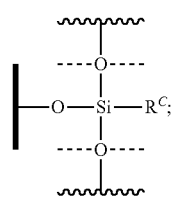

wherein $R^C$ is selected from:
(i) $C_{1-24}$alkyl, wherein one or more available carbon atoms in the alkyl are optionally replaced by —O— or —S—;
(ii) $C_{1-24}$alkylene—O—C(O)CF$_3$, wherein one or more available carbon atoms in the alkylene are optionally replaced by —O— or —S—; and
(iii) $C_{1-24}$alkylene-OH, wherein one or more available carbon atoms in the alkylene are optionally replaced by —O— or —S—;

▬ represents the surface of the solid support; and each ⋅⋅⊖⋅⋅ represents an oxygen atom in the siloxane network.

6. The method of claim 5, wherein $R^C$ is hexyl, octadecyl or 3-(2-(2,2,2-trifluoroacetoxy)ethoxy)propyl.

7. The method of claim 1, wherein the dye-modified actin is rhodamine-modified actin.

8. The method of claim 1, wherein the dye-modified actin is N-hydroxysuccinimide(NHS)-rhodamine-modified actin.

9. The method of claim 1, wherein $R^C$ is octyl.

10. The method of claim 1, wherein
   (a) the solid support comprises plastic, glass, metal, metal oxide or crystal, and the solid support is in the form of a testing strip, a well in a microwell plate or a microcentrifuge tube; or
   (b) the solid support comprises or consists essentially of silica gel or comprises magnetic nanoparticles, and the silica gel or magnetic nanoparticles are housed in a column, vial or tube.

11. The method of claim 10, wherein the solid support is in the form of a microcentrifuge tube.

12. The method of claim 1, wherein the method quantifies the amount of LPA in a liquid sample, and comprises:
   exposing a first portion of the sample to a first biosensor;
   analyzing the first portion of the sample after exposure to the first biosensor to obtain a first signal value;
   adding a known amount of LPA to a second portion of the sample;
   exposing the second portion of the sample to a second biosensor;
   analyzing the second portion of the sample after exposure to the second biosensor to obtain a second signal value;
   exposing a third portion of the sample to a control made of the same solid support as the biosensors but not the dual protein system or linker;
   analyzing the third portion of the sample after exposure to the control to obtain a control signal value; and
   calculating the ratio of the first signal value minus the control signal value to the second signal value minus the control signal value to determine the concentration of LPA that was present in the sample,
   wherein the first biosensor and the second biosensor are each made of the same solid support, and dual protein system and linker; and
   wherein the steps of analyzing comprise spectroscopically measuring a signal associated with the dye of the dye-modified actin.

13. The method of claim 1, wherein the method quantifies the amount of LPA in a liquid sample, and comprises:
   exposing a first portion of the sample to a first biosensor;
   analyzing the first portion of the sample after exposure to the first biosensor to obtain a first signal value;
   adding different known amounts of LPA to each of a plurality of additional portions of the sample;
   exposing each of the plurality of additional portions of the sample to a respective plurality of additional biosensors;
   analyzing each of the plurality of additional portions of the sample after exposure to the respective plurality of additional biosensors to obtain a plurality of additional signal values;
   plotting the signal value obtained for each portion of the sample against the corresponding concentration of LPA added to the portion of the sample; and
   obtaining the concentration of LPA that was present in the sample from the y-intercept of the line of best fit for the plot,
   wherein the steps of analyzing comprise spectroscopically measuring a signal associated with the dye of the dye-modified actin.

14. The method of claim 1, wherein the actin is modified with a dye suitable for detection by UV-visible absorbance spectroscopy and the step(s) of analyzing comprise(s) measuring, by ultraviolet-visible absorbance spectroscopy, a signal associated with said dye or wherein the actin is modified with a dye suitable for detection by fluorescence spectroscopy and the step(s) of analyzing comprise(s) measuring, by fluorescence spectroscopy, a signal associated with said dye.

15. The method of claim 1, wherein the liquid sample is a serum sample from a subject, wherein the subject is a woman over the age of fifty and/or wherein the woman has a family history of ovarian cancer, wherein the concentration of LPA in the serum sample is determined to be above about 1.5 µM and the method further comprises determining whether or not the subject has ovarian cancer by a method which comprises using an imaging technique.

16. The method of claim 15, wherein the imaging technique comprises transvaginal ultrasound (TVU).

* * * * *